US012788977B2

(12) United States Patent
Frieding et al.

(10) Patent No.: US 12,788,977 B2
(45) **Date of Patent: *Nov. 10, 2026**

(54) USER INTERFACES OF A HEARING DEVICE

(71) Applicant: Cochlear Limited, Macquarie University (AU)

(72) Inventors: Jan Patrick Frieding, Grose Vale (AU); Ivana Popovac, Dee Why (AU)

(73) Assignee: Cochlear Limited, Macquarie University (AU)

( * ) Notice: Subject to any disclaimer, the term of this patent is extended or adjusted under 35 U.S.C. 154(b) by 122 days.

This patent is subject to a terminal disclaimer.

(21) Appl. No.: 18/739,855

(22) Filed: Jun. 11, 2024

(65) Prior Publication Data

US 2024/0325746 A1 Oct. 3, 2024

Related U.S. Application Data

(63) Continuation of application No. 18/625,466, filed on Apr. 3, 2024, which is a continuation-in-part of
(Continued)

(51) Int. Cl.
*H04R 25/00* (2006.01)
*A61N 1/36* (2006.01)
(Continued)

(52) U.S. Cl.
CPC ........... *A61N 1/36* (2013.01); *A61N 1/36038* (2017.08); *A61N 1/36039* (2017.08);
(Continued)

(58) Field of Classification Search
CPC ..... A61F 11/00; H04R 2225/41; H04R 25/00; H04R 25/305; H04R 25/43; H04R 25/554; H04R 25/558; H04R 25/603; H04R 25/70
(Continued)

(56) References Cited

U.S. PATENT DOCUMENTS

| | | | |
|---|---|---|---|
| 7,092,763 | B1 | 8/2006 | Griffith et al. |
| 7,529,587 | B2 | 5/2009 | Single |

(Continued)

FOREIGN PATENT DOCUMENTS

| | | | |
|---|---|---|---|
| EP | 0823829 A2 | 2/1998 | |
| KR | 10-2011-0011394 | 2/2011 | |
| WO | 11/110228 A1 | 9/2011 | |

OTHER PUBLICATIONS

Extended European Search Report in corresponding European Application No. 15847056.7, mailed Feb. 5, 2018, 5 pages.

(Continued)

*Primary Examiner* — Phylesha Dabney
(74) *Attorney, Agent, or Firm* — Edell, Shapiro & Finnan, LLC

(57) ABSTRACT

Presented herein are techniques for dynamically changing how a recipient-associated device (e.g., external component and/or user device linked to an external component) interacts with a user based on whether the external component of a medical device system is coupled to the recipient. In particular, a recipient-associated device in accordance with embodiments presented herein provides a first type of user interaction while the external component is coupled to the recipient, but the recipient-associated device provides a second (and different) type of user interaction when the external component is uncoupled/decoupled from the recipient (e.g., dynamically adjusting a user interface provided by a recipient-associated device based on whether the external component is coupled or decoupled from the recipient).

8 Claims, 13 Drawing Sheets

Related U.S. Application Data application No. 17/189,481, filed on Mar. 2, 2021, now abandoned, which is a continuation of application No. 16/202,495, filed on Nov. 28, 2018, now Pat. No. 10,967,176, which is a continuation of application No. 15/584,666, filed on May 2, 2017, now Pat. No. 10,148,809, which is a continuation of application No. 14/867,741, filed on Sep. 28, 2015, now Pat. No. 9,643,018.

(60) Provisional application No. 62/058,079, filed on Sep. 30, 2014.

(51) Int. Cl.

| | |
|---|---|
| ***A61N 1/372*** | (2006.01) |
| ***H04M 1/72478*** | (2021.01) |
| *A61F 11/00* | (2022.01) |

(52) U.S. Cl.

CPC .... *A61N 1/37247* (2013.01); *H04M 1/72478* (2021.01); *H04R 25/305* (2013.01); *H04R 25/43* (2013.01); *H04R 25/554* (2013.01); *A61F 11/00* (2013.01); *H04Q 2213/002* (2013.01); *H04Q 2213/107* (2013.01); *H04Q 2213/381* (2013.01); *H04R 25/00* (2013.01); *H04R 2225/41* (2013.01)

(58) Field of Classification Search

USPC .......................................................... 381/314

See application file for complete search history.

(56) References Cited

U.S. PATENT DOCUMENTS

| | | | | |
|---|---|---|---|---|
| 7,747,030 | B2 | 6/2010 | Fink et al. | |
| 7,860,261 | B2 | 12/2010 | Beilin | |
| 8,437,860 | B1 | 5/2013 | Crawford et al. | |
| 8,983,100 | B2 | 3/2015 | Tinaphong | |
| 9,124,991 | B2 * | 9/2015 | van Gerwen | H04R 25/43 |
| 9,124,994 | B2 | 9/2015 | Corti et al. | |
| 9,155,900 | B2 | 10/2015 | Meskens | |
| 9,232,320 | B2 | 1/2016 | Hartley et al. | |
| 9,264,821 | B2 | 2/2016 | Thiede et al. | |
| 9,491,530 | B2 | 11/2016 | Karunasiri | |
| 9,643,018 | B2 | 5/2017 | Frieding et al. | |
| 9,781,524 | B2 | 10/2017 | Olsen et al. | |
| 10,148,809 | B2 | 12/2018 | Frieding et al. | |
| 10,456,577 | B2 | 10/2019 | Calle et al. | |
| 10,967,176 | B2 | 4/2021 | Frieding et al. | |
| 2004/0073275 | A1 | 4/2004 | Maltan et al. | |
| 2005/0078846 | A1 * | 4/2005 | Single | H04R 25/505 381/326 |
| 2008/0165994 | A1 | 7/2008 | Caren et al. | |
| 2008/0288022 | A1 | 11/2008 | Van der Borght et al. | |
| 2009/0264963 | A1 | 10/2009 | Faltys et al. | |
| 2010/0272299 | A1 | 10/2010 | Van Schuylenbergh et al. | |
| 2012/0029594 | A1 | 2/2012 | Chapa et al. | |
| 2012/0226331 | A1 | 9/2012 | Banna et al. | |
| 2013/0029594 | A1 | 1/2013 | Shimado | |
| 2013/0039519 | A1 | 2/2013 | Kilsgaard et al. | |
| 2013/0308803 | A1 | 11/2013 | Hartley et al. | |
| 2014/0010378 | A1 | 1/2014 | Voix et al. | |
| 2014/0135871 | A1 | 5/2014 | Meskens | |
| 2014/0155686 | A1 | 6/2014 | Meskens | |
| 2015/0223539 | A1 | 8/2015 | Marco | |
| 2018/0295457 | A1 * | 10/2018 | van Gerwen | H04R 25/43 |
| 2021/0252284 | A1 | 8/2021 | Frieding et al. | |

OTHER PUBLICATIONS

Written Opinion and International Search Report from International Application No. PCT/IB2015/002138, dated Mar. 24, 2016.

* cited by examiner

COUPLED STATE

DECOUPLED STATE

DECOUPLED STATE

USER INTERFACES OF A HEARING DEVICE

CROSS-REFERENCE TO RELATED APPLICATIONS

This is a continuation of U.S. patent application Ser. No. 18/625,466, filed Apr. 3, 2024, which is a continuation-in-part of U.S. patent application Ser. No. 17/189,481, filed Mar. 2, 2021, which is a continuation of U.S. patent application Ser. No. 16/202,495, filed Nov. 28, 2018, now U.S. Pat. No. 10,967,176, which is a continuation of U.S. patent application Ser. No. 15/584,666, filed on May 2, 2017, now U.S. Pat. No. 10,148,809, which is a continuation of U.S. patent application Ser. No. 14/867,741, filed on Sep. 28, 2015, now U.S. Pat. No. 9,643,018, which claims priority from U.S. Provisional Application No. 62/058,079, filed Sep. 30, 2014. These earlier applications are incorporated herein by reference in their entirety.

BACKGROUND

Field of the Invention

The present invention relates generally to user interfaces of implantable medical devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: determining, by at least one processor, whether a state of a hearing device unit is either in (i) a coupled state in which the hearing device is being worn by a person or (ii) an uncoupled state in which the hearing device unit is not being worn by a person; providing, via a user interface component, a first user interface when the determined state is the coupled state; and providing, via the user interface component, a second user interface when the determined state is the uncoupled state, wherein the second user interface provides access to at least one hearing device function that is not available via first user interface.

In another aspect, a hearing device system is provided. The hearing device system comprises: an external unit configured to be worn by a recipient; a sound processor configured to process audio input and to provide associated hearing-stimulation output; at least one user-interface component; a wireless communication interface; and at least one processor configured to determine whether the external unit is in a coupled state when the external unit is being worn by the recipient or an uncoupled state when the hearing device unit is not being worn by the recipient, wherein the at least one user-interface component is configured to provide a first user interface when the external unit is worn on the body of the user and (ii) a second user interface when the external unit is not worn on the body of the user, and wherein functionalities provided via the second user interface differ from functionalities provided via the first user interface.

In another aspect, a hearing device system is provided. The hearing device system comprises: a hearing prosthesis configured to have a coupled state in which the hearing prosthesis is worn on the body of a user of the hearing prosthesis and an uncoupled state in which the hearing prosthesis is not worn on the body of the user; at least one user interface component; a wireless communication interface wherein the at least one user-interface component is configured to provide a first user interface when the hearing prosthesis is in the coupled state, and a second user interface when the hearing prosthesis is in the uncoupled state, wherein functionalities provided via the second user interface differ from functionalities provided via the first user interface.

In another aspect, a method is provided. The method comprises: determining whether an external component of an implantable medical device system is either in (i) a coupled state in which the external component is being worn by a recipient or (ii) a decoupled state in which the external component is not being worn by a recipient; providing, with at least one recipient-associated device linked with the external component, a first type of user-interaction when the determined state is the coupled state; and providing, with the at the one or more recipient-associated device, a second type of user-interaction when the determined state is the decoupled state.

BRIEF DESCRIPTION OF THE DRAWINGS

Embodiments of the present invention are described herein in conjunction with the accompanying drawings, in which.

DETAILED DESCRIPTION

Figure 1B:
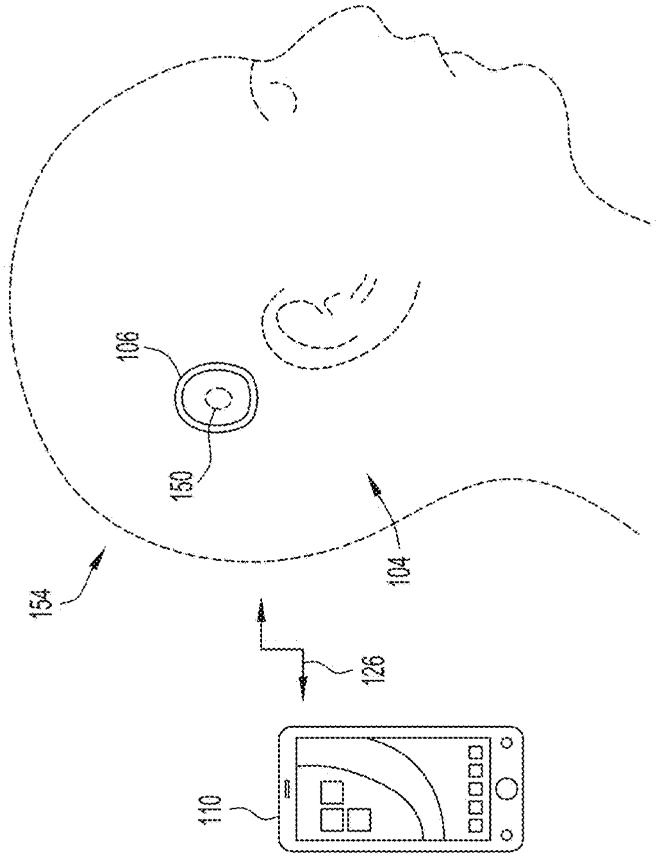
FIG. 1B is a side view of a recipient wearing a sound processing unit of the cochlear implant system of FIG. 1A.

A number of medical device systems include one or more external units/components that operate with an implantable unit/component. When in use, the external component(s) is/are configured to be coupled to the recipient to communicate with the implantable component, to provide power to the implantable component, etc. The external component(s) can be configured to be physically attached to, or worn by, the recipient and/or the external component(s) can be configured to be magnetically coupled to the implantable component. As used herein, an external component "coupled to" a recipient includes an external component that is physically attached to the recipient, an external component that is worn by the recipient, and/or an external component that is magnetically coupled to an implantable component disposed in the recipient. In certain examples, the external component (s) and/or the implantable component can also be "linked" or "associated" with another device, such as a mobile phone or wearable device, which are collectively and generally referred to herein as "user devices." For ease of description, the term "recipient-associated devices" is used to refer to refer to user devices and external components.

In general, a recipient-associated device, whether it is an external component, a mobile phone, a smartwatch, etc., has the ability to interact with a user (e.g., the recipient, caregiver, clinician, or another person). In certain examples, the interaction can occur via a user interface that allows the user to receive information from the associated device and/or enter information into the associated device. In other examples, the interaction can occur via an audible or tactile mechanism that is separate from a user interface. Presented herein are techniques for dynamically changing how a recipient-associated device (e.g., external component and/or user device linked to an external component) interacts with a user based on whether the external component of a medical device system is coupled to the recipient. In particular, a recipient-associated device in accordance with embodiments presented herein provides a first type of user interaction while the external component is coupled to the recipient, but the recipient-associated device provides a second (and different) type of user interaction when the external component is uncoupled/decoupled from the recipient (e.g., dynamically adjusting a user interface provided by a recipient-associated device based on whether the external component is coupled or decoupled from the recipient).

For ease of description, the term "linked recipient-associated device" is used to refer to a recipient-associated device (e.g., external component or separate second device) that is configured so as to be notified, either directly or indirectly, when an external device is decoupled from, or conversely when coupled to, a recipient. Stated differently, a recipient-associated device is referred to as being "linked" or "associated" with an external component when the recipient-associated device is notified of a change in the coupling state of the external component. It is to be appreciated, however, that the term linked recipient-associated device does not require or imply that the device is separate from the external component. To the contrary, the term linked recipient-associated device includes the external component itself that is coupled/decoupled from the recipient, as well as any separate devices that are linked to the external component that is coupled/decoupled (i.e., associated such that the separate device is notified when the component that is coupled/decoupled from the recipient).

There are a number of different types of devices in/with which embodiments of the present invention may be implemented. Merely for ease of description, the techniques presented herein are primarily described with reference to a specific device in the form of a cochlear implant system. However, it is to be appreciated that the techniques presented herein may also be partially or fully implemented by any of a number of different types of devices, including consumer electronic device (e.g., mobile phones), wearable devices (e.g., smartwatches), hearing devices, implantable medical devices, consumer electronic devices, etc. As used herein, the term "hearing device" is to be broadly construed as any device that acts on an acoustical perception of an individual, including to improve perception of sound signals, to reduce perception of sound signals, etc. In particular, a hearing device can deliver sound signals to a user in any form, including in the form of acoustical stimulation, mechanical stimulation, electrical stimulation, etc., and/or can operate to suppress all or some sound signals. As such, a hearing device can be a device for use by a hearing-impaired person (e.g., hearing aids, middle car auditory prostheses, bone conduction devices, direct acoustic stimulators, electro-acoustic hearing prostheses, auditory brainstem stimulators, bimodal hearing prostheses, bilateral hearing prostheses, dedicated tinnitus therapy devices, tinnitus therapy device systems, combinations or variations thereof, etc.), a device for use by a person with normal hearing (e.g., consumer devices that provide audio streaming, consumer headphones, earphones, and other listening devices), a hearing protection device, etc. In other examples, the techniques presented herein can be implemented by, or used in conjunction with, various implantable medical devices, such as visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1A:
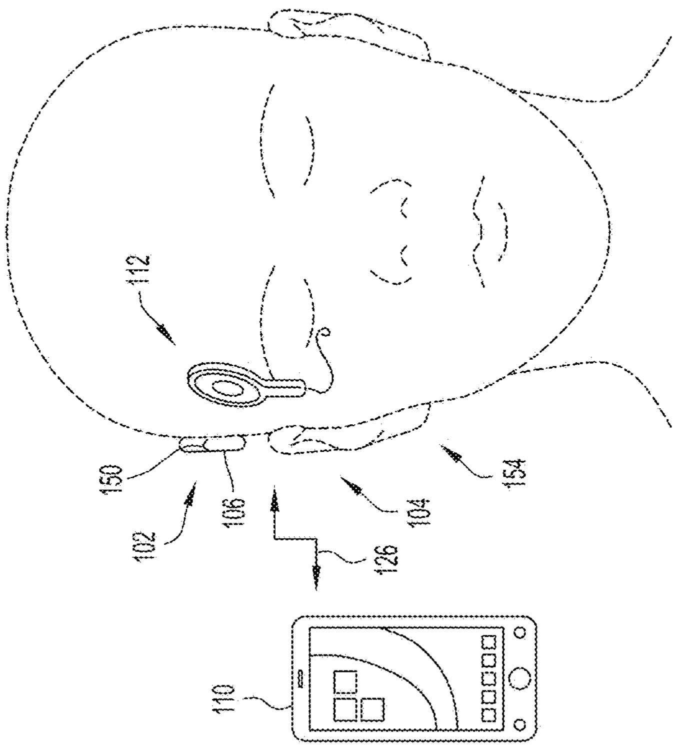
FIG. 1A is a schematic diagram illustrating a cochlear implant system with which aspects of the techniques presented herein can be implemented.
Figure 1C:
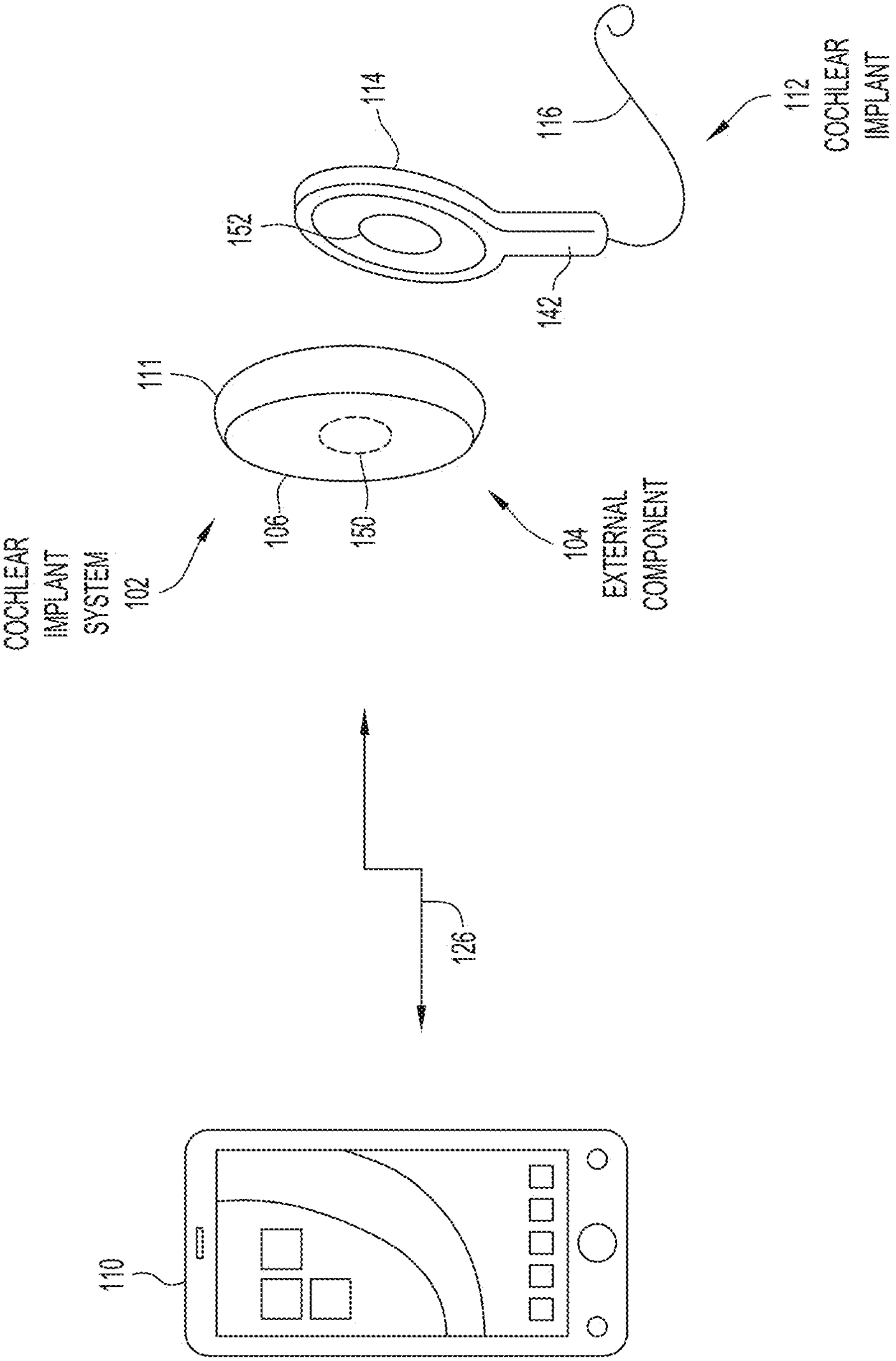
FIG. 1C is a schematic view of components of the cochlear implant system of FIG. 1A.
Figure 1D:
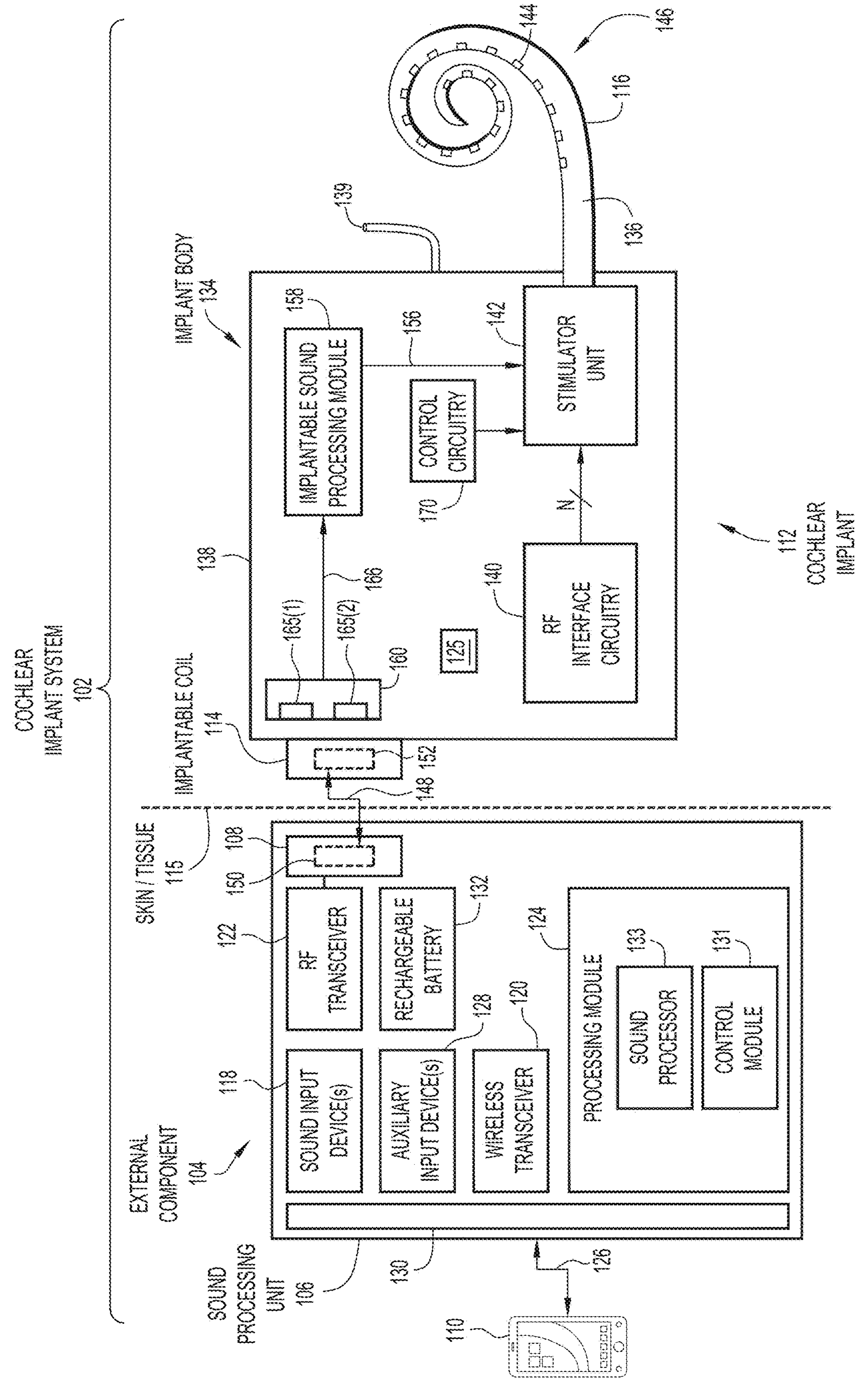
FIG. 1D is a block diagram of the cochlear implant system of FIG. 1A.

FIGS. 1A-1D illustrate an example cochlear implant system 102 with which aspects of the techniques presented herein can be implemented. The cochlear implant system 102 comprises an external component 104 that is configured to be directly or indirectly coupled to the recipient, and an internal/implantable component 112 that is configured to be implanted in or worn on the head of the recipient. In the examples of FIGS. 1A-1D, the implantable component 112 is sometimes referred to as a "cochlear implant." FIG. 1A illustrates the cochlear implant 112 implanted in the head 154 of a recipient, while FIG. 1B is a schematic drawing of the external component 104 worn on the head 154 of the recipient. FIG. 1C is another schematic view of the cochlear implant system 102, while FIG. 1D illustrates further details of the cochlear implant system 102. For case of description, FIGS. 1A-ID will generally be described together.

In the examples of FIGS. 1A-1D, the external component 104 comprises a sound processing unit 106, an external coil 108, and generally, a magnet fixed relative to the external coil 108. The cochlear implant 112 includes an implantable coil 114, an implant body 134, and an elongate stimulating assembly 116 configured to be implanted in the recipient's cochlea. In one example, the sound processing unit 106 is an off-the-ear (OTE) sound processing unit, sometimes referred to herein as an OTE component, that is configured to send data and power to the implantable component 112. In general, an OTE sound processing unit is a component having a generally cylindrically shaped housing 111 and which is configured to be magnetically coupled to the recipient's head 154 (e.g., includes an integrated external magnet 150 configured to be magnetically coupled to an internal/implantable magnet 152 in the implantable component 112). The OTE sound processing unit 106 also includes an integrated external (headpiece) coil 108 (the external coil 108) that is configured to be inductively coupled to the implantable coil 114.

It is to be appreciated that the OTE sound processing unit 106 is merely illustrative of the external devices that could operate with implantable component 112. For example, in alternative examples, the external component 104 may comprise a behind-the-ear (BTE) sound processing unit configured to be attached to, and worn adjacent to, the recipient's ear. A BTE sound processing unit comprises a housing that is shaped to be worn on the outer car of the recipient. In certain examples, the BTE is connected to a separate external coil assembly via a cable, where the external coil assembly is configured to be magnetically and inductively coupled to the implantable coil 114, while in other embodiments the BTE includes a coil disposed in or on the housing worn on the outer car of the recipient. It is also to be appreciated that alternative external components could be located in the recipient's ear canal, worn on the body, etc.

Although the cochlear implant system 102 includes the sound processing unit 106 and the cochlear implant 112, as described below, the cochlear implant 112 can operate independently from the sound processing unit 106, for at least a period, to stimulate the recipient. For example, the cochlear implant 112 can operate in a first general mode, sometimes referred to as an "external hearing mode," in which the sound processing unit 106 captures sound signals which are then used as the basis for delivering stimulation signals to the recipient. The cochlear implant 112 can also operate in a second general mode, sometimes referred as an "invisible hearing" mode, in which the sound processing unit 106 is unable to provide sound signals to the cochlear implant 112 (e.g., the sound processing unit 106 is not present, the sound processing unit 106 is powered-off, the sound processing unit 106 is malfunctioning, etc.). As such, in the invisible hearing mode, the cochlear implant 112 captures sound signals itself via implantable sound sensors and then uses those sound signals as the basis for delivering stimulation signals to the recipient. Further details regarding operation of the cochlear implant 112 in the external hearing mode are provided below, followed by details regarding operation of the cochlear implant 112 in the invisible hearing mode. It is to be appreciated that reference to the external hearing mode and the invisible hearing mode is merely illustrative and that the cochlear implant 112 could also operate in alternative modes.

Figure 1E:
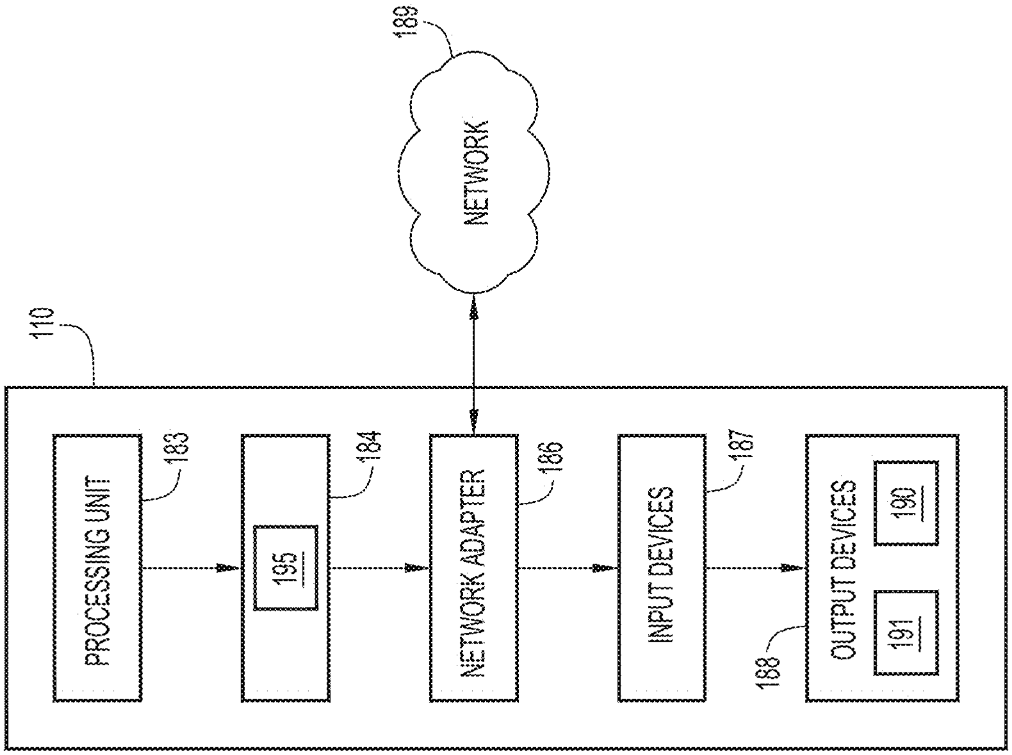
FIG. 1E is a schematic diagram illustrating a computing device with which aspects of the techniques presented herein can be implemented.

In FIGS. 1A and 1C, the cochlear implant system 102 is shown with an external device 110, configured to implement aspects of the techniques presented. The external device 110, which is shown in greater detail in FIG. 1E, is a computing device, such as a personal computer (e.g., laptop, desktop, tablet), a mobile phone (e.g., smartphone), a remote control unit, etc. The external device 110 and the cochlear implant system 102 (e.g., sound processing unit 106 or the cochlear implant 112) wirelessly communicate via a bi-directional communication link 126. The bi-directional communication link 126 may comprise, for example, a short-range communication, such as Bluetooth link, Bluetooth Low Energy (BLE) link, a proprietary link, etc.

Returning to the example of FIGS. 1A-1D, the sound processing unit 106 of the external component 104 also comprises one or more input devices configured to capture and/or receive input signals (e.g., sound or data signals) at the sound processing unit 106. The one or more input devices include, for example, one or more sound input devices 118 (e.g., one or more external microphones, audio input ports, telecoils, etc.), one or more auxiliary input devices 128 (e.g., audio ports, such as a Direct Audio Input (DAI), data ports, such as a Universal Serial Bus (USB) port, cable port, etc.), and a short-range wireless transmitter/receiver (wireless transceiver) 120 (e.g., for communication with the external device 110), each located in, on or near the sound processing unit 106. However, it is to be appreciated that one or more input devices may include additional types of input devices and/or less input devices (e.g., the short-range wireless transceiver 120 and/or one or more auxiliary input devices 128 could be omitted).

The sound processing unit 106 also comprises the external coil 108, a charging coil 130, a closely-coupled radio frequency transmitter/receiver (RF transceiver) 122, at least one rechargeable battery 132, a user interface module 175, and a processing module 124. The processing module 124 can be configured to perform a number of operations that are represented in FIG. 1D by a control module 131 and a sound processor 133. The control module 131 and sound processor 133 can each be formed by one or more processors (e.g., one or more Digital Signal Processors (DSPs), one or more uC cores, etc.), firmware, software, etc. arranged to perform operations described herein. That is, the control module 131 and sound processor 133 can each be implemented as firmware elements, partially or fully implemented with digital logic gates in one or more application-specific integrated circuits (ASICs), partially or fully in software, etc.

Returning to the example of FIGS. 1A-1D, the implantable component 112 comprises an implant body (main module) 134, a lead region 136, and the stimulating assembly 116, all configured to be implanted under the skin (tissue) 115 of the recipient. The implant body 134 generally comprises a hermetically-sealed housing 138 that includes, in certain examples, at least one power source 125 (e.g., one or more batteries, one or more capacitors, etc.), in which the RF interface circuitry 140 and a stimulator unit 142 are disposed. The implant body 134 also includes the internal/implantable coil 114 that is generally external to the housing 138, but which is connected to the RF interface circuitry 140 via a hermetic feedthrough (not shown in FIG. 1D).

As noted, the stimulating assembly 116 is configured to be at least partially implanted in the recipient's cochlea. The stimulating assembly 116 includes a plurality of longitudinally spaced intra-cochlear electrical stimulating contacts (electrodes) 144 that collectively form a contact array (electrode array) 146 for delivery of electrical stimulation (current) to the recipient's cochlea. The stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 150 is fixed relative to the external coil 108 and the internal/implantable magnet 152 is fixed relative to the implantable coil 114. The external magnet 150 and the internal/implantable magnet 152 fixed relative to the external coil 108 and the internal/implantable coil 114, respectively, facilitate the operational alignment of the external coil 108 with the implantable coil 114. This operational alignment of the coils enables the external component 104 to transmit data and power to the implantable component 112 via a closely-coupled wireless link 148 formed between the external coil 108 with the implantable coil 114. In certain examples, the closely-coupled wireless link 148 is an RF link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, the sound processing unit 106 includes the processing module 124. The processing module 124 is configured to process the received input audio signals (received at one or more of the input devices, such as sound input devices 118 and/or auxiliary input devices 128) and convert the received input audio signals into output control signals for use in stimulating a first car of a recipient or user (i.e., the processing module 124 is configured to perform sound processing on input signals received at the sound processing unit 106). Stated differently, the one or more processors (e.g., processing element(s) implementing firmware, software, etc.) in the processing module 124 are configured to execute sound processing logic in memory to convert the received input audio signals into output control signals (stimulation signals) that represent electrical stimulation for delivery to the recipient.

As noted, FIG. 1D illustrates an embodiment in which the processing module 124 in the sound processing unit 106 generates the output control signals. In an alternative embodiment, the sound processing unit 106 can send less processed information (e.g., audio data) to the implantable component 112, and the sound processing operations (e.g., conversion of input sounds to output control signals 156) can be performed by a processor within the implantable component 112.

In FIG. 1D, according to an example embodiment, output control signals (stimulation signals) are provided to the RF transceiver 122, which transcutaneously transfers the output control signals (e.g., in an encoded manner) to the implantable component 112 via the external coil 108 and the implantable coil 114. That is, the output control signals (stimulation signals) are received at the RF interface circuitry 140 via the implantable coil 114 and provided to the stimulator unit 142. The stimulator unit 142 is configured to utilize the output control signals to generate electrical stimulation signals (e.g., current signals) for delivery to the recipient's cochlea via one or more of the stimulating contacts 144. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the input audio signals (the received sound signals).

As detailed above, in the external hearing mode, the cochlear implant 112 receives processed sound signals from the sound processing unit 106. However, in the invisible hearing mode, the cochlear implant 112 is configured to capture and process sound signals for use in electrically stimulating the recipient's auditory nerve cells. In particular, as shown in FIG. 1D, an example embodiment of the cochlear implant 112 can include a plurality of implantable sound sensors 165(1), 165(2) that collectively form a sensor array 160, and an implantable sound processing module 158. Similar to the processing module 124, the implantable sound processing module 158 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

In the invisible hearing mode, the implantable sound sensors 165(1), 165(2) of the sensor array 160 are configured to detect/capture input sound signals 166 (e.g., acoustic sound signals, vibrations, etc.), which are provided to the implantable sound processing module 158. The implantable sound processing module 158 is configured to convert received input sound signals 166 (received at one or more of the implantable sound sensors 165(1), 165(2)) into output control signals 156 for use in stimulating the first car of a recipient or user (i.e., the implantable sound processing module 158 is configured to perform sound processing operations). Stated differently, the one or more processors (e.g., processing element(s) implementing firmware, software, etc.) in the implantable sound processing module 158 are configured to execute sound processing logic in memory to convert the received input sound signals 166 into output control signals 156 that are provided to the stimulator unit 142. The stimulator unit 142 is configured to utilize the output control signals 156 to generate electrical stimulation signals (e.g., current signals) for delivery to the recipient's cochlea, thereby bypassing the absent or defective hair cells that normally transduce acoustic vibrations into neural activity.

It is to be appreciated that the above description of the so-called external hearing mode and the so-called invisible hearing mode are merely illustrative and that the cochlear implant system 102 could operate differently in different embodiments. For example, in one alternative implementation of the external hearing mode, the cochlear implant 112 could use signals captured by the sound input devices 118 and the implantable sound sensors 165(1), 165(2) of sensor array 160 in generating stimulation signals for delivery to the recipient.

FIG. 1E is a block diagram illustrating one example arrangement for an external computing device (user device) 110 configured to perform one or more operations in accordance with certain embodiments presented herein. As shown in FIG. 1E, in its most basic configuration, the external computing device 110 includes at least one processing unit 183 and a memory 184. The processing unit 183 includes one or more hardware or software processors (e.g., Central Processing Units) that can obtain and execute instructions. The processing unit 183 can communicate with and control the performance of other components of the external computing device 110. The memory 184 is one or more software or hardware-based computer-readable storage media operable to store information accessible by the processing unit 183. The memory 184 can store, among other things, instructions executable by the processing unit 183 to implement applications or cause performance of operations described herein, as well as other data. The memory 184 can be volatile memory (e.g., RAM), non-volatile memory (e.g., ROM), or combinations thereof. The memory 184 can include transitory memory or non-transitory memory. The memory 184 can also include one or more removable or non-removable storage devices. In examples, the memory 184 can include RAM, ROM) EEPROM (Electronically-Erasable Programmable Read-Only Memory), flash memory, optical disc storage, magnetic storage, solid state storage, or any other memory media usable to store information for later access. By way of example, and not limitation, the memory 184 can include wired media, such as a wired network or direct-wired connection, and wireless media, such as acoustic, RF, infrared, other wireless media, or combinations thereof. In certain embodiments, the memory 184 comprises logic 195 that, when executed, enables the processing unit 183 to perform aspects of the techniques presented.

In the illustrated example of FIG. 1E, the external computing device 110 further includes a network adapter 186 and a user interface module (user interface) 185 that includes one or more user-interface components, including user input components/devices 187, and one or more output devices 188. The external computing device 110 can include other components, such as a system bus, component interfaces, a graphics system, a power source (e.g., a battery), among other components. The network adapter 186 is a component of the external computing device 110 that provides network access (e.g., access to at least one network 189). The network adapter 186 can provide wired or wireless network access and can support one or more of a variety of communication technologies and protocols, such as Ethernet, cellular, Bluetooth, near-field communication, and RF, among others. The network adapter 186 can include one or more antennas and associated components configured for wireless communication according to one or more wireless communication technologies and protocols. The one or more input devices 187 are devices over which the external computing device 110 receives input from a user. The one or more input devices 187 can include physically-actuatable user-interface elements (e.g., buttons, switches, or dials), a keypad, keyboard, mouse, touchscreen, and voice input devices, among other input devices that can accept user input. The one or more output devices 188 are devices by which the external computing device 110 is able to provide output to a user. The output devices 188 can include a display 190 (e.g., a liquid crystal display (LCD)) and one or more speakers 191, among other output devices for presentation of visual or audible information to the recipient, a clinician, an audiologist, or other user.

It is to be appreciated that the arrangement for the external computing device 110 shown in FIG. 1E is merely illustrative and that aspects of the techniques presented herein can be implemented at a number of different types of recipient devices including any combination of hardware, software, and/or firmware configured to perform the functions described herein. For example, the external computing device 110 can be a personal computer (e.g., a desktop or laptop computer), a hand-held device (e.g., a tablet computer), a mobile device (e.g., a smartphone), a wearable device, and/or any other electronic device having the capabilities to perform the associated operations described elsewhere herein.

As noted above, presented herein are techniques for changing how a recipient-associated device (e.g., external component and/or user device) interacts with a user based on whether the external component of the medical device system is coupled to the recipient. Accordingly, in certain aspects of the techniques presented herein, a determination is made as to whether an external component of a medical device system is in a coupled stated (e.g., when the external component and the stimulation unit are magnetically coupled) or a decoupled state (e.g., when the external component and the stimulation unit are not magnetically coupled). A recipient-associated device interacts with a user in a first manner (e.g., provides a first user interface) when the determined state is the coupled state, and interacts with a user in a second manner (e.g., provides a second user interface) when the determined state is the decoupled state.

By way of example, the user interface of an external component can include one or more input/output (I/O) components configured to receive user inputs and/or to provide visual displays of information. The visual displays may take any number of forms, such as, for instance, different lights or light patterns, or even a graphical user interface. When the recipient is able to view the output components, e.g., when the external component is decoupled from the recipient's body, the external component provide the recipient with the ability to review and change a number of parameters associated with both processing functions. As a result of these interactions, the external component may provide the recipient with a number of visual displays (e.g., status displays) representative of settings for sound-processing parameters and/or other parameters. Such visual displays may help the recipient to select a particular parameter and to verify the changes being made to such parameter.

When the recipient is wearing the external component, however, the recipient may have a limited ability to perceive visual displays. As a result, the external component may not provide as many visual displays, if any at all, when the external component is coupled to the recipient. Similarly, the external component may provide fewer input functions when the external component is coupled to the recipient, as compared to the input functions available when the external component is decoupled from the recipient.

Adapting the functions associated with the user interface based on whether the external component is coupled to or decoupled from the recipient may enhance a recipient's experience with the medical device system when the output components are visible to the recipient while conserving power resources when they are not. Limiting the number of visual displays when the output components are not visible to the recipient may also avoid situations in which a visual display unnecessarily draws attention to the recipient's external component or is otherwise irrelevant to an observer. Further, providing a limited number of functions while the external component is coupled to the recipient could also reduce a likelihood of the recipient accidentally applying an incorrect change to a parameter setting while the recipient is unable to visually verify the setting. On the other hand, providing a wide range of functions when the external component is decoupled from the recipient can give the recipient more options for adapting the operations of the device to the recipient's individual preferences.

Similarly, providing a limited number of visual outputs when the external component is coupled to the recipient—and thus when the recipient's ability to perceive visual displays is reduced—may conserve power for processing. Whereas when the external component is decoupled from the recipient, providing a greater number of visual outputs may deliver more information regarding different aspects of the operations of the device, thereby enhancing the recipient's ability to interact with and customize the operations.

As noted, the techniques presented herein can also be used dynamically adjust how a recipient-associated device (e.g., external component, mobile phone, wearable device, etc.) interacts with a recipient based on whether an external component of a medical device is coupled or decoupled from a recipient. By way of example, the user interface of a user device can include one or more input/output (I/O) components configured to receive user inputs and/or to provide visual displays of information. The visual displays may take any number of forms, such as, for instance, different lights or light patterns, or even a graphical user interface. In these examples, the output components of the user device user interface can provide a certain type of information (e.g., information about the implantable component) when the external component is coupled to the recipient, but a different type of information (e.g., information about the external component) when the external component is decoupled to the recipient. As detailed further below, other types of interactions are also within the scope of the techniques presented herein.

Figure 2:
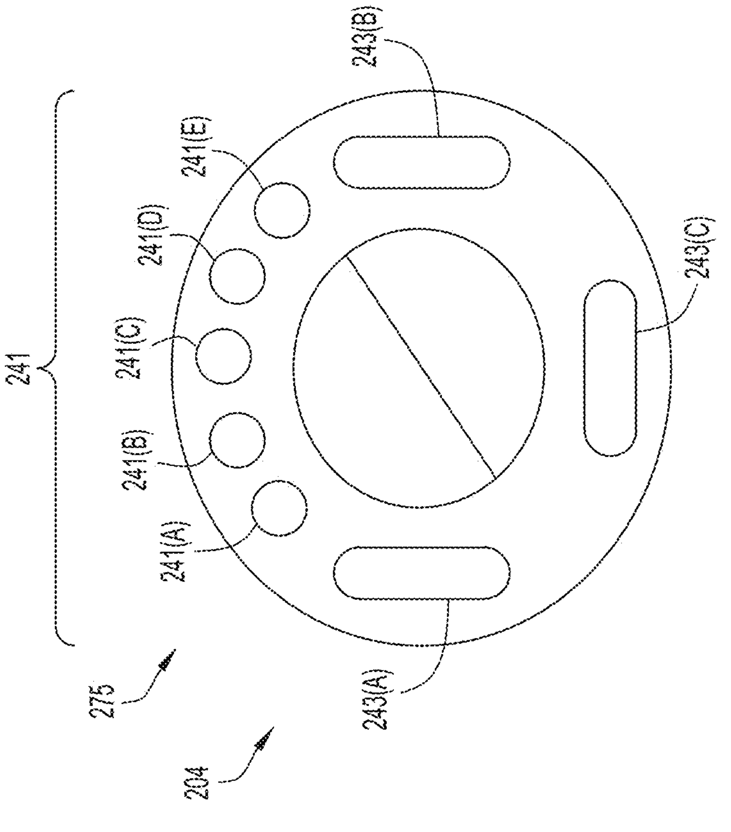
FIG. 2 is a schematic diagram illustrating an external component of an implant system, in accordance with certain embodiments presented herein.

FIG. 2 is a schematic diagram illustrating one example embodiment of an external component, such external component 104, in accordance with certain embodiments presented herein. In the example of FIG. 2 the external component is referred to as external components 204 and, merely for ease of description, is described with reference to components of cochlear implant system 102 of FIGS. 1A-1D.

In the example of FIG. 2, the external component 104 operates in one of two states: a coupled state and a decoupled state. When operating in the coupled state (e.g., worn by the recipient), the external components 204 processes sounds, generates stimulation data, and sends the stimulation data to cochlear implant 112. That is, coupling the external component 104 to the cochlear implant 112 facilitates transmission of data between the respective external component and the as cochlear implant 112, perhaps by aligning a coil 108 (FIGS. 1A-ID) of the external component 104A/104B with a coil 114 of the as cochlear implant 112. Typically, coupling is achieved via the magnets 150 and 152 included in the external component 104A/104B and the cochlear implant 112, respectively. However, other means for coupling the external component 104A/104B and the cochlear implant 112 are possible as well. When the recipient decouples the external component 104 from the cochlear implant 112, the external component 104 is in the decoupled state.

The external component 104 provides the recipient, or perhaps a different user, with one or more user interfaces via the user interface module 275. As used herein, a "user interface module" is comprised of one or more "user-interface components" or "user-interface devices," which can comprise any I/O component that assists the recipient in interacting with the associated device. In addition, the term "user interface" is used herein to refer the audible, visible and tactile inputs and/or outputs provided by a user interface module (e.g., provided by the user-interface components).

Returning to the example of FIG. 2, each user interface allows the recipient to interact with the external component 104 to review and/or change parameters associated with operations of the cochlear implant system 102. The parameters can include, for example, sound-processing parameters used by a sound processor when generating stimulation signals, such as a volume of perceived sounds (e.g., an amplitude of stimuli applied by the cochlear implant 112), a sound-processing strategy, a current sound-processing profile, fault codes, and/or the like. The parameters may also include system parameters that are not specifically related to sound-processing functions, such as a battery level (e.g., a current charge of the battery), usage information, alarm times, or the like.

To facilitate this interaction, the one or more user-interface components may include at least one user-input component and at least one display component. By way of example, FIG. 2 depicts the external component 104 as including a light emitting diode (LED) array 241 and three buttons 243A, 243B, and 243C. In the example arrangement, the LED array 241 includes five LEDs 241A, 241B, 241C, 241D, and 241E. In alternative arrangements, however, the external component 104 may include more or fewer than five LEDs and/or three buttons. Moreover, the external component 104 may include, in lieu of one or more of the buttons 243A-243C, one or more different user-input components, such as one or more switches, a resistive-touch device, a capacitive-touch device, and or any other user-input component suitable for inclusion on the external component 104.

In the example arrangement, the external component 104 receive user-inputs via one or more of the buttons 243A-243C and provides visual outputs, or displays of information, via the LED array 241. In practice, functionalities of the buttons 243A-243C and/or the LED array 241 depends on whether the external component 104 is in the coupled state or the decoupled state.

In an example implementation of the user interface in the decoupled state, the recipient may press a left button 243(A) or a right button 243(C) to scroll through a set of parameters of the cochlear implant system 102, which includes both sound-processing parameters and system parameters. As the recipient scrolls through the set of parameters, the external component 104 may cause the LED array 241 to provide a visual output in response to each interaction. As one example, the external component 104 may cause one or more of the LEDs to light, with a number and/or pattern of the LEDs 241A-241E corresponding to a particular parameter.

For instance, for the first five parameters, the external component 104 may cause one of the LEDs 241A-241E to light as a corresponding parameter is selected. By way of example, a first LED 241A may correspond to a first parameter, a second LED 241B may correspond to a second parameter, etc. For additional parameters, multiple LEDs 241A-241E may light. For instance, the first LED 241A and the second LED 241B may light to represent a sixth parameter, the first LED 241A and a third LED 241C may light to represent a seventh parameter, etc. Thus, the example LED array 241 can provide visual outputs representing up to thirty-one individual parameters. Further, in an example in which each LED 241A-241E in the LED array 241 can light in different colors, the LED array 241 could provide visual outputs for more than thirty-one individual parameters. In practice, however, the recipient will likely have access to fewer than thirty-one individual parameters.

Each parameter may correspond to a sound-processing parameter or a system parameter. The recipient may then press an enter button 243(C) to select one of the parameter. The LED array 241 may responsively provide a visual output indicative of a current setting of the selected parameter. If the selected parameter is a current volume setting, for example, a number of the LEDs representative of the current volume setting may light. In this example, lighting each of the LEDs 241A-241E may indicate a maximum volume setting, and lighting none of the LEDs 241A-241E may indicate a minimum volume setting.

As another example, each sound-processing profile may be associated with a particular lighting pattern of one or more LEDs 241A-241E. For example, a first sound-processing profile may be associated with the first LED 241A lighting, a second sound-processing profile may be associated with the second LED 241B lighting, etc. If the selected parameter is a current sound-processing profile (i.e., the sound-processing profile that the external component 104 will use to generate stimulation signals), the external component 104 may cause the one or more of the LEDs 241A-241E to light based on the current sound-processing profile, thereby providing a visual indication of the current sound-processing profile. Other examples of sound-processing parameters are possible as well.

The recipient can also select a system parameter to get an indication of a status of the selected system parameter. For example, if the recipient selects a system parameter corresponding to a battery level, the external component 104 may provide a visual output indicative of the current battery level, perhaps by lighting each of the LEDs 241A-241E when the battery is completely charged (e.g., the battery level is at approximately 100%) or lighting none of the LEDs 241A-241E when the battery is nearly drained (e.g., the battery level approaching 10%). Additionally or alternatively, the external component 104 may cause one or more of the LEDs 241A-241E to light in one color, such as green, when the battery level is above a threshold battery level, and the external component 104 may cause one or more of the LEDs 241A-241E to light in a different color, such as red, when the battery level is below the threshold level. Other examples of system parameters are also possible.

The recipient can also interact with one or more of the buttons 243A-243C to change the setting of some parameters. To change the volume, for example, the recipient may press the right button 243(B) to increase the volume or the left button 243(A) to decrease the volume. The LED array 241 may provide a visual output representative of the new volume as the recipient presses the buttons 243(A), 243(B). And when the recipient has set the volume to the desired level, the recipient may press the enter button 243(C) to apply the new volume setting. Alternatively, the external component 104 may automatically apply the new volume setting, or another selected parameter, if the recipient subsequently couples the external component 104 to the cochlear implant 112 without pressing the enter button 243(C). Further, if the recipient does not press the enter button 243(C) within a period of time, the external component 104 may not apply the new volume.

When the external component 104 is in the decoupled state, the LED array 241 may also automatically provide visual outputs in some conditions. For example, upon entering the decoupled state, i.e., when the recipient decouples the external component 104 from the cochlear implant 112, the LED array 241 may automatically display a current parameter setting, such as the battery level. Further, the recipient may be able to select the parameter that is automatically displayed upon decoupling, perhaps by interacting with the one or more buttons 243A-243C. Additionally or alternatively, the LED array 241 may also automatically provide an indication of a fault or error detected by the external component 104, perhaps by causing one or more of the LEDs 241A-241E to flash and/or light in red.

In one example implementation, the external component 104 provides a limited user interface when the external component 104 is idled. For example, if a recipient interaction is not received within a time limit, such as perhaps thirty seconds or even several minutes, the external component 104 is idled. In this case, none of the LEDs 241 may be lit, thereby conserving the power resources of the external component's battery. Or if the external component 104 is charging, the LED array 241 may provide a visual output indicative of the charging and/or a current charging level, perhaps by flashing or lighting one or more of the LEDs 241A-241E in a left-to-right sequence.

To "wake up" the external component 104 from the idled condition, the recipient may interact with the external component 104, perhaps by pressing one of the buttons 243A-243C, thereby providing the recipient with access to the full user interface available in the decoupled state. Additionally or alternatively, the recipient can wake up the external component 104 by moving the external component 104. In this example, the external component 104 may include one or more sensors configured to detect a movement of the external component 104, such as one or more accelerometers. In this case, the external component 104 could determine whether a movement detected by the one or more sensors is consistent with the recipient preparing to interact with the device, such as when the recipient picks the external component 104 up from a table. In yet a further example, the external component 104 could be configured to wake up when the recipient unplugs a charging cable.

In the coupled state, the external component 104 provides a different user interface. The recipient may have a limited, if any, ability to see the LED array 241 while wearing the external component 104. Accordingly, the user interface generally provides fewer visual outputs in the coupled state than in the decoupled state. And since the recipient typically needs to modify only one or two parameters, most notably the volume, while wearing the external component 104, the user interface also provides access to fewer functions than it does in the decoupled state. Further, because the recipient does not receive visual feedback when the external component is in the coupled state, limiting the functionalities corresponding to inputs may also reduce a likelihood of the recipient accidentally changing the wrong parameter.

The external component 104 may thus provide a user interface in the coupled state that allows the recipient to change fewer parameters than in the decoupled state. For example, pressing the left button 243(A) or the right button 243(B) may respectively decrease or increase the volume setting, as opposed to scrolling through a series of selectable parameters, as described with respect to the user interface in the decoupled state. In an additional example, the recipient may also be able to cycle through the available sound-processing modes or profiles by pressing the enter button 243(B).

Additionally, whereas the external component 104 may provide a visual output in response to the recipient interacting with one of the buttons 243(A)-243(C) when in the decoupled state, the external component 104 may not provide a visual output in response to such interactions in the coupled state. Instead, the external component 104 may generate, and send to the cochlear implant 112, one or more stimulation signals that provide an audible indication of the change being applied. For example, when the recipient increases the volume, the external component 104, upon applying the change, may generate stimulation signals that will cause the recipient to perceive a tone, with a volume of the tone being representative of the maximum volume. Additionally, if the recipient changes a sound-processing mode or profile, the resulting stimulation signals generated by the external component 104 may cause the recipient to perceive a tone, or perhaps a spoken word or phrase indicative of the selected sound-processing mode/profile.

In some examples, however, the external component 104 may still provide visual outputs in the coupled state. For instance, the external component 104 may cause one of the LEDs 241A-241E to provide visual indication of whether the cochlear implant system 102 is properly functioning. As one example, one of the LEDs, such as the third LED 241C, may be lit, or possibly flash, green when the cochlear implant system 102 is operating normally or red when the cochlear implant system 102 is not operating normally. The third LED 241C may also flash red when the battery level is low. Additionally, the external component 104 may be equipped with an external speaker, in which case the external component 104 may also provide an audible alarm when the cochlear implant system 102 is not functioning properly. These indications may be particularly advantageous when the recipient is a student, as the visual indication may alert a teacher when the recipient is using the cochlear implant system 102 and/or when the cochlear implant system 102 is not properly operating.

The recipient could also configure the external component 104, perhaps by using an external computing device, to cause the LEDs 241A-241E to be lit while the recipient is wearing the external component 104 in certain locations. In the example in which the recipient is a student, for instance, the external component 104 may be configured to limit visual outputs while in the coupled state to times in which the recipient is at school. Additionally or alternatively, the external component 104 may include a positioning device, such as a global positioning service (GPS) receiver. The external component 104 could also be configured to receive a signal indicative of a current location of the recipient, perhaps by receiving positioning information from a local area wireless network or a positioning device, such as a device with a GPS receiver. In these examples, the external component 104 may provide visual outputs only in certain locations while in the coupled state, such as when the external component 104 determines that the recipient is at school.

Figure 3:
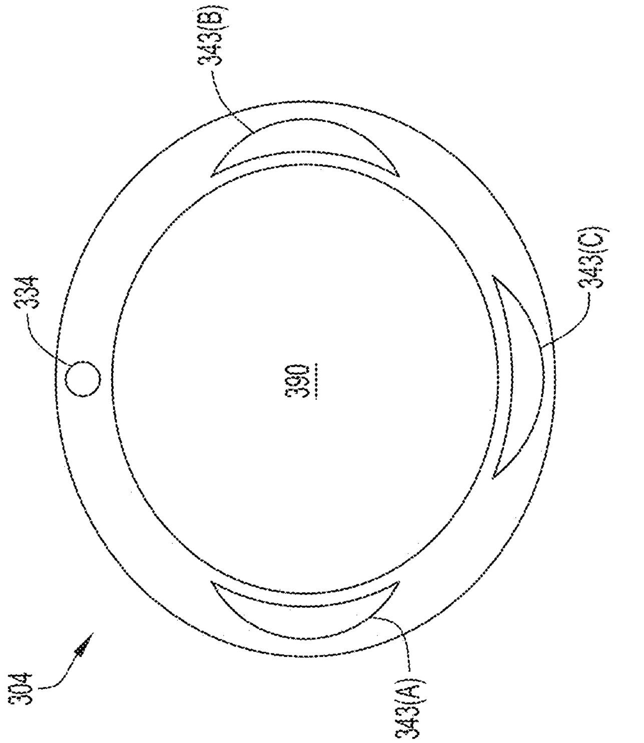
FIG. 3 is a schematic diagram illustrating another external component of an implant system, in accordance with certain embodiments presented herein.

FIG. 3 illustrates another example external component 304. The external component 304 includes a display 290, a sensor 334, and buttons 343(A), 343(B), and 343(C). The display 390 is preferably an electronic paper display, perhaps implemented as a touchscreen, though the display 390 could also be a liquid crystal display (LCD) or an LED display. The buttons 343(A), 343(B), and 343(C) are substantially similar to the buttons 243(A), 243(B), and 243(C), respectively. Further, in lieu of one or more of the buttons, the external component 304 can include one or more different user-input components, such as one or more switches, a resistive-touch device, a capacitive-touch device, and or any other suitable user-input component.

The sensor 334 can provide an additional indication of the recipient interacting with the external component 304. The external component 304 may periodically receive from the sensor 334 a signal indicative of whether the recipient is looking at the display 390. For instance, the external component 304 may be idled if a signal indicative of the recipient is looking at the display 390 is not received within a time limit, such as thirty seconds or up to several minutes. Additionally or alternatively, the external component 304 may not wake up until both a signal from the sensor 334 indicative of the recipient looking at the device and a user-input at one of the buttons 343(A)-343(C) are received.

Like the external component 104, the external component 304 can provide a user interface in the decoupled state that differs from the user interface in the coupled state. The recipient may interact with the user interface, in both the decoupled state and the coupled state, in a manner that is the same as or substantially similar to the interactions described with respect to the external component 104. The visual outputs provided by the external component 304, however, differ from those provided by the external component 104.

In the decoupled state, for instance, the external component 304 provides a user interface, such as a graphical user interface, that includes one or more interactive menus capable of being displayed on the display 390. Each menu may include one or more parameters, thereby allowing the recipient to quickly access a particular parameter. A representation of each such menu, and any submenus, and of each parameter may depend in part on the size of the display 390. For example, a representation of a parameter could be an abbreviation, such as "VOL" for volume or "BAT" for battery level, or a graphic or an image representative of the parameter, such as a graphic of a speaker for volume or a graphic of a battery for battery level.

The external component 304 may also provide more information than the external component 104 provides regarding the operation of the cochlear implant system 102. For example, the recipient can select information regarding the recipient's usage of the implant (e.g., the time periods or amount of time in which recipient used the stimulation unit provided stimuli to the recipient), fault or error codes and times such codes were received, and, if the cochlear implant 112 includes an independent battery, the battery level of the cochlear implant 112.

The display 390 may also provide visual outputs while the external component is idled in the decoupled state. While the external component 304 is charging, for example, the display 390 may provide a graphic of a battery that is representative of the current battery level, and perhaps an amount of time needed to fully charge the battery. The display 390 may also display an indication of whether the external component 304 is calibrated for the recipient's right ear or left ear, perhaps by displaying an "R" or an "L," which may be helpful if the recipient uses two hearing devices.

Further, in still another example, the display 390 may provide recipient-identifying information, such as the recipient's name and telephone number, if the external component 304 is idled. If the recipient misplaces the external component, this information can help a person who finds the external component 304 in returning it to the recipient. Alternatively, rather than providing the recipient-identifying information, the display 390 could display an identification code and telephone number for a third-party service that will assist the finder in returning the external component 304. When the external component 304 receives location information, again from either a wireless network of from a positioning device, the recipient-identifying information may be displayed in certain locations, while the more discreet identification code and phone number are displayed in other locations. In this manner, the recipient can designate certain areas in which to display the recipient-identifying information, such as in areas where a prospective finder is more likely to know or be able to quickly identify the recipient. Examples of such areas may include a school or a work place.

Like the external component 104, the external component 304, when in the coupled state, may not provide an output indicative of a setting or status of a parameter. Instead, the external component 304 may cause the display 390 to provide a visual output unrelated to hearing device operations or functions. For instance, the external component 304 might cause the display 390 to provide a display that approximates the recipient's hair pattern. Such a display may be predetermined and stored in a data storage of the external component 304, and the external component 304 may access the data storage to provide the display. This may provide some camouflaging of the external component 304, thereby making it less apparent to people around the recipient that the recipient is wearing the external component 304. Alternatively, the recipient might configure the display 390 to display a personal graphic or image, such as a logo of a sports team. And in some examples, the external component 304 may include an LED, such as the LED 241(C) described with respect to the external component 104, which the external component 304 may light to provide a visual indication of whether the cochlear implant system 102 is properly functioning. In certain examples, when the external component 304 is removed from the head, the user interface changes from an "on-head inconspicuous" arrangement to an "off-head informative" arrangement.

Figure 4:
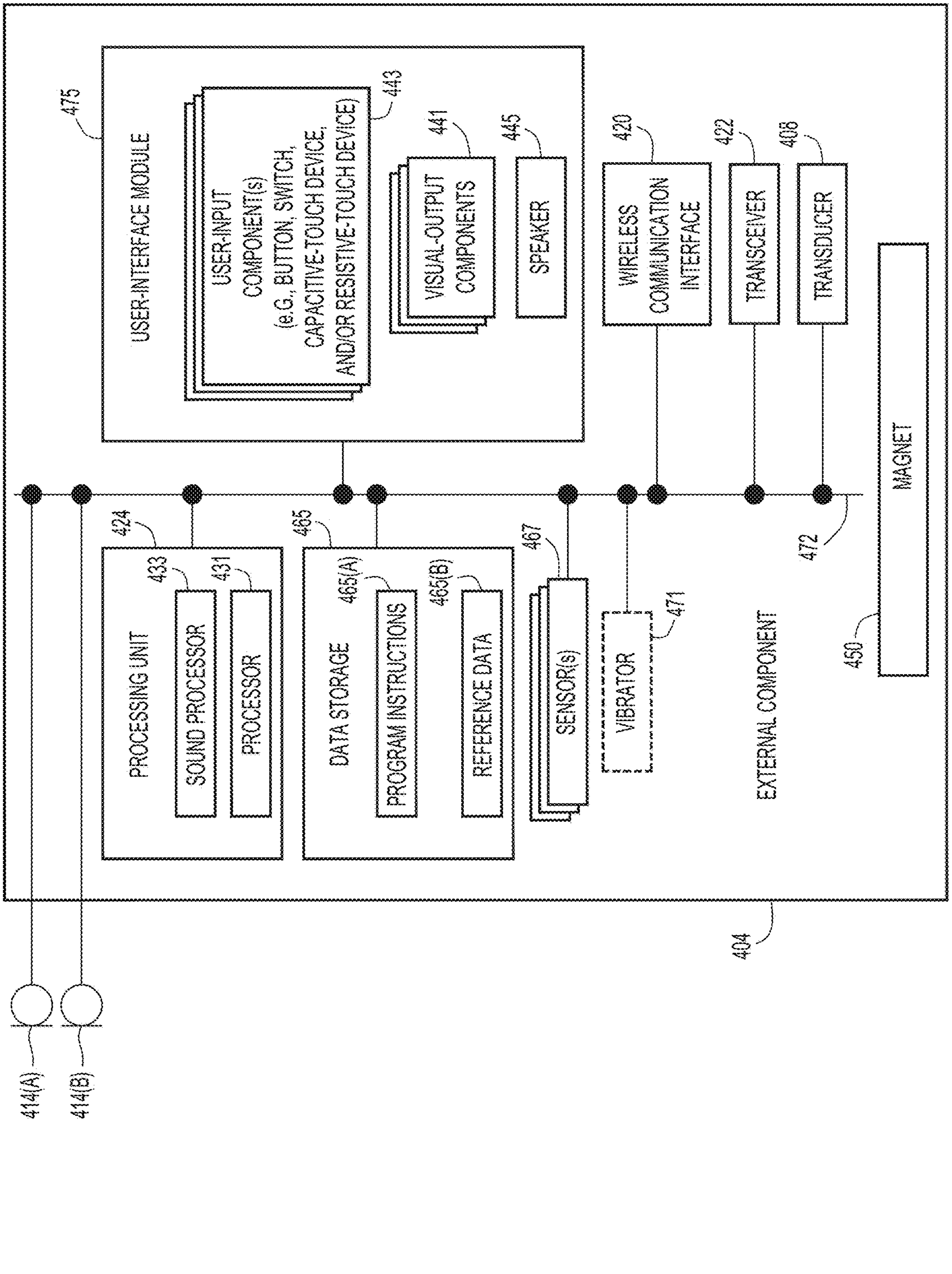
FIG. 4 is a block diagram of an external component of an implant system, in accordance with certain embodiments presented herein.

FIG. 4 is functional bock diagram illustrating further details of an external component, referred to as external component 404, in accordance with certain embodiments presented. It is to be appreciated that the external component 404 could operate with any of a number of different implantable components (implantable medical devices). As such, the arrangement of external component 404 shown in FIG. 4 is merely illustrative and that an external component in accordance with embodiments presented herein could include additional functional components and/or could omit one or more of the components shown in FIG. 4.

In the example shown in FIG. 4, the external component 404 includes a user-interface module 475, microphones (or other audio transducers) 418(A) and 418(B), a processing module/unit 424, data storage 465, one or more sensor(s) 467, a wireless communication interface 420, and a transceiver 422, which are communicatively linked together by a system bus, network, or other connection mechanism 472. The external component 404 also includes a magnet 450, thereby allowing the external component 404 to magnetically couple to an implantable component (e.g., cochlear implant 112), and a transducer 408, such as an inductive coil, that is electrically connected to the transceiver 422 to facilitate communications with the implantable component.

In an example arrangement, the components shown in FIG. 4 are included in a single housing. In alternative arrangements, the components could be provided in or more physical units for use by the recipient. For example, the microphones 418(A) and 418(B), the processing unit 124, the data storage 465, the wireless communication interface 420, the user-interface module 475, and the transceiver 442 may be included in a behind-the-ear housing. The magnet 450 and the transducer 408, and perhaps one or more sensors 467, may be included in a separate housing that is connected to the first housing by a cable. Other arrangements are possible as well.

The user-interface module 475 includes one or more user-interface components suitable for providing user interfaces to the recipient. As shown in FIG. 4, the user-interface module 475 includes one or more user-input components 443, one or more visual-output components 441, and a speaker 445. The one or more user-input components 443 may be the same as or substantially similar to the buttons 243(A)-243(C) or 343(A)-343(C) described with respect to FIGS. 2 and 3, respectively. Similarly, the one or more visual-output components 441 may be the same as or substantially similar to the LED array 241 and/or the display 390 described with respect to FIGS. 2 and 3, respectively. Note that in some examples, the user-interface module 475 may include a touchscreen, which could constitute both one of the one or more user-input components 443 and one of the one or more visual-output components 441.

In certain examples, when the external component 404 is in the coupled state, the speaker 445 may provide one or more audible alarms when the associated implantable component is not operating properly. The alarm may be a tone, a tone pattern, or a melody, or perhaps a spoken phrase or an audible indication of a particular fault experienced by the implantable component. When the external component 404 is in the decoupled state, the speaker 445 may provide audible outputs in response to an interaction with one of the one or more user-input components 443. The speaker 445 could also provide an audible alarm that indicates the external component 404 needs to be charged and/or an indication of the external component 404 being lost or misplaced. Other example outputs are possible as well.

In the arrangement as shown, the microphones 418(A) and 418(B) are configured to receive audio signals/inputs, such as audio coming from an acoustic environment, and to provide a corresponding signal (e.g., electrical or optical, possibly sampled) to the processing unit 424. For instance, the microphones 418(A) and 418(B) could be positioned on an exposed surface of the housing of the external component 104. Further, the microphones 418(A) and 418(B) may comprise additional microphones and/or other audio transducers, which could also be positioned on an exposed surface of the housing of the external component 404.

The processing unit 424 can comprise one or more processors (e.g., microprocessors) and/or one or more special purpose processors (e.g., application-specific integrated circuits, programmable logic devices, etc.). As shown, at least one such processor functions as a sound processor 433 to process received audio input so as to enable generation of corresponding stimulation signals. Further, another such processor 431 could be configured to receive and process inputs received via the one or more user-input components 443 and to provide outputs via the one or more visual-output components 441. The processor 433 may also receive and process signals received via the one or more sensors 467, perhaps via the user-interface module 475, and to responsively determine whether the external component 404 is coupled to or decoupled from the implantable component, and/or to determine whether the recipient has interacted with the external component 404 within a time limit. Further, the processor 433 may cause the speaker 445 to provide an audible output, perhaps in response to determining the implantable component is not operating properly. Alternatively, all processing functions, including functions for implementing the user interfaces, could be carried out by the sound processor 433.

The data storage 465 may then comprise one or more volatile and/or non-volatile storage components, such as magnetic, optical, or flash storage, and may be integrated in whole or in part with processing unit 424. As shown, the data storage 465 may hold program instructions 465(A) executable by the processing unit 424 to carry out various hearing device functions described herein, as well as reference data 465(B) that the processing unit 424 may reference as a basis to carry out various such functions.

By way of example, the program instructions 465(A) may be executable by the processing unit 424 to provide one or more user interfaces. For instance, the program instructions may include instructions for providing a first user interface in the coupled state and a second user interface in the decoupled state. To this end, the instructions may cause the processing unit 424 to process a user input by performing a function selected from either a first set of functions when in the coupled state or a second set of functions when in the decoupled state, with the second of set of functions differing from the first set of functions. The first set of functions may provide, for instance, the recipient with the ability to directly adjust one or two sound-processing parameters, whereas the second set of functions may provide the recipient with the ability to cycle through a number of additional sound-processing parameters, as well as one or more system parameters, review settings such parameters, and change one or more of the settings.

Similarly, the instructions may cause the processing unit 424 to provide a visual output selected from either a first set of visual outputs when in the coupled state or a second set of visual outputs when in the decoupled state. Consistent with the above discussion, the second set of visual outputs includes a greater number of visual outputs than the first set of visual outputs. That is, because the recipient has the ability to access more sound-processing parameters, as well as system parameters, via the second user interface, the second user interface provides a wider variety of visual outputs than the first set of visual outputs. The instructions may further cause the processing unit 424 to automatically provide a visual output or, in the decoupled state, to provide a visual output in response to an interaction with the external component 404.

The reference data 465(B) may include settings of adjustable sound-processing parameters, such as a current volume setting, a current recipient profile, and/or a current number of channels per signal, and static sound-processing parameters, such as, for instance, multiple recipient profiles. Moreover, the reference data 465(B) may include settings of system parameters not associated with sound-processing operations, such as one or more alarm times and/or recipient usage information. The processing unit 424 may access the reference data 465(B) to determine a current status or setting of a parameter prior to producing a visual output in the decoupled state. Additionally, the processing unit 424 may change a setting of a sound-processing parameter or a system parameter when performing a recipient-request function. Note that the listed examples of parameters are illustrative in nature and do not represent an exclusive list of possible sound-processing parameters and/or system parameters.

The one or more sensors 467 may provide the processing unit 424 with one or more signals indicative of whether the external component 404 is coupled to or decoupled from the implantable component. To this end, the one or more sensors 467 may include a sensor configured to provide an output in the presence of a magnetic field, such as a Reed switch or a Hall effect sensor. Such a sensor may provide an output to the processing unit 424 in the presence of a magnetic field generated by the magnet 450 and a magnet included in the implantable component.

The one or more sensors 467 may also include one or more sensors configured to detect a movement or condition indicative of the recipient is interacting with the external component 404. As previously described, the one or more sensors could include one or more accelerometers, an infrared emitter/detector, a camera, or perhaps even an internal positioning system. As another example, the one or more sensors 467 could include an audio sensor (e.g., a microphone). In this case, the one or more sensors 467 may receive verbal commands from the recipient, and the processing unit 424 may process a received verbal command to display a status of and/or update a parameter of the external component 104. The one or more sensors 467 may include one or more other types of sensors as well. Note that in some examples, however, the external component 404 may not include the one or more sensors 467.

The wireless communication interface 420 may then comprise a wireless chipset and antenna, arranged to pair with and engage in wireless communication with a corresponding wireless communication interface in another device such as wireless network of an external device, according to an agreed protocol such as one of those noted above. For instance, the wireless communication interface 420 could be a BLUETOOTH radio and associated antenna or could take other forms. In these examples, the wireless communications may include relaying data associated with a location of the recipient, which the wireless communication interface 420 may relay to the processing unit 424 in order to assist the processing unit 424 in selecting a visual output to provide via the one or more visual-output components 441. Note that like the one more sensors 467, the external component 404 may not include the wireless communication interface 420 in each possible embodiment.

As noted above, the techniques presented herein can be implemented with a number of different systems that include an implantable component and an external component configured to be at least temporarily coupled to a recipient. For example, the techniques presented herein could be implemented with cochlear implants, middle car auditory prostheses, bone conduction devices, direct acoustic stimulators, electro-acoustic hearing prostheses, auditory brainstem stimulators, bimodal hearing prostheses, bilateral hearing prostheses, dedicated tinnitus therapy devices, tinnitus therapy device systems, combinations or variations thereof, etc. visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

In addition, it is to be appreciated that the external component can have a number of different arrangements and/or can provide different functions for the system. For example, as described above, in certain embodiments the external component can be a processing device that provides data to an implantable component. In certain embodiments, the external component can provide both data and power to the implantable component. In still other embodiments, the external component can be a charging device/component (charger) that primarily provides power to the implantable component. The external component can be configured to be coupled to the recipient for extended periods of time or for only discrete periods of time.

In one illustrative example, an external component in accordance with embodiments operates with a vestibular implant (e.g., provides power and/or data to a vestibular implant). In such examples, the external component could display different information, depending on whether the external component is coupled to the recipient. For example, while coupled to the recipient (e.g., when worn on the head), the external component could display a degree of efficiency (in real time), a degree of body motion speed relative to device efficiency, a spirit level, etc. However, when decoupled from the recipient, the external component could provide a results readout, data captured while in use, etc.

In certain examples, the external component includes one or more microphones that, when the external component is coupled to the recipient, are configured to receive/capture sound signals. However, in accordance with certain embodiments presented herein, while the external component is decoupled from the recipient, the microphones can operate as a "tap" interface that enables the recipient to adjust settings or modes of the external component and/or implantable component (e.g., if the external component and implantable component can communicate with one another via a wireless connection other than a closely-coupled link). In a similar embodiment, the external component could include or one more user-input components (e.g., tap interface/button(s)/capacitive touch interface, etc.) that are disabled when the external component is coupled to the recipient, but enabled when the external component is decoupled from the recipient. Such an arrangement could, for example, act to prevent erroneous inputs while in use (e.g., from scratching, due to physical activity, etc.).

FIGS. 2, 3, and 4 have been described with reference to providing different user interfaces at an external component (e.g., external component 104, 304, or 404), depending on whether the external component is coupled to, or decoupled from, the recipient (e.g., different pushbuttons, lights, private alerts, etc. at the external component). As noted above, the use of different interfaces is only one example technique in which an external component (or another recipient-associated device) can provide different user interactions, depending on whether the external component is coupled to, or decoupled from, the recipient.

For example, in one arrangement, the external component 404 includes a vibrator 471 (shown using a dashed box) that facilities different interactions with the recipient, depending on whether the external component is coupled or decoupled from the recipient. More specifically, if the external component 404 is a bone conduction device, then the vibrator 471 could be used to deliver stimulation signals (mechanical vibrations) to the recipient when the external component 404 is coupled to recipient (e.g., the vibrator 471 vibrators in accordance with data generated, by the sound processor 433, from sound signals received by the microphones 418(1)/418(B)). However, in such an arrangement, when the external component 404 is removed from the head, the vibrator is configured to generate notification vibrations. For example, removing the external component 404 could trigger vibrations (e.g., after a period of time) to remind the user that the component is not in use, to indicate a battery status (e.g., the battery is running low), to indicate phone call is being received at a paired phone, for locating the device (e.g., "lost mode"), etc. It would be appreciated that these specific notification vibrations are merely illustrative and that other vibrations can be generated when the external component 404 is removed from the head of a recipient.

FIGS. 2, 3, and 4 also generally illustrate examples in which an external component (e.g., external component 104, 304, or 404) itself is configured to provide a different type of user interaction based on whether or not the external component of a medical device system is coupled to the recipient. That is, in the above embodiments, the interaction between the recipient and the external component itself is dynamically changed depending on whether the external component is coupled to, or decoupled from, the recipient. As noted above, in accordance with certain embodiments presented herein, the coupling status/state of the external component could also or alternatively be used to dynamically adjust how a second "linked" device interacts with the recipient or other user.

Figure 5A:
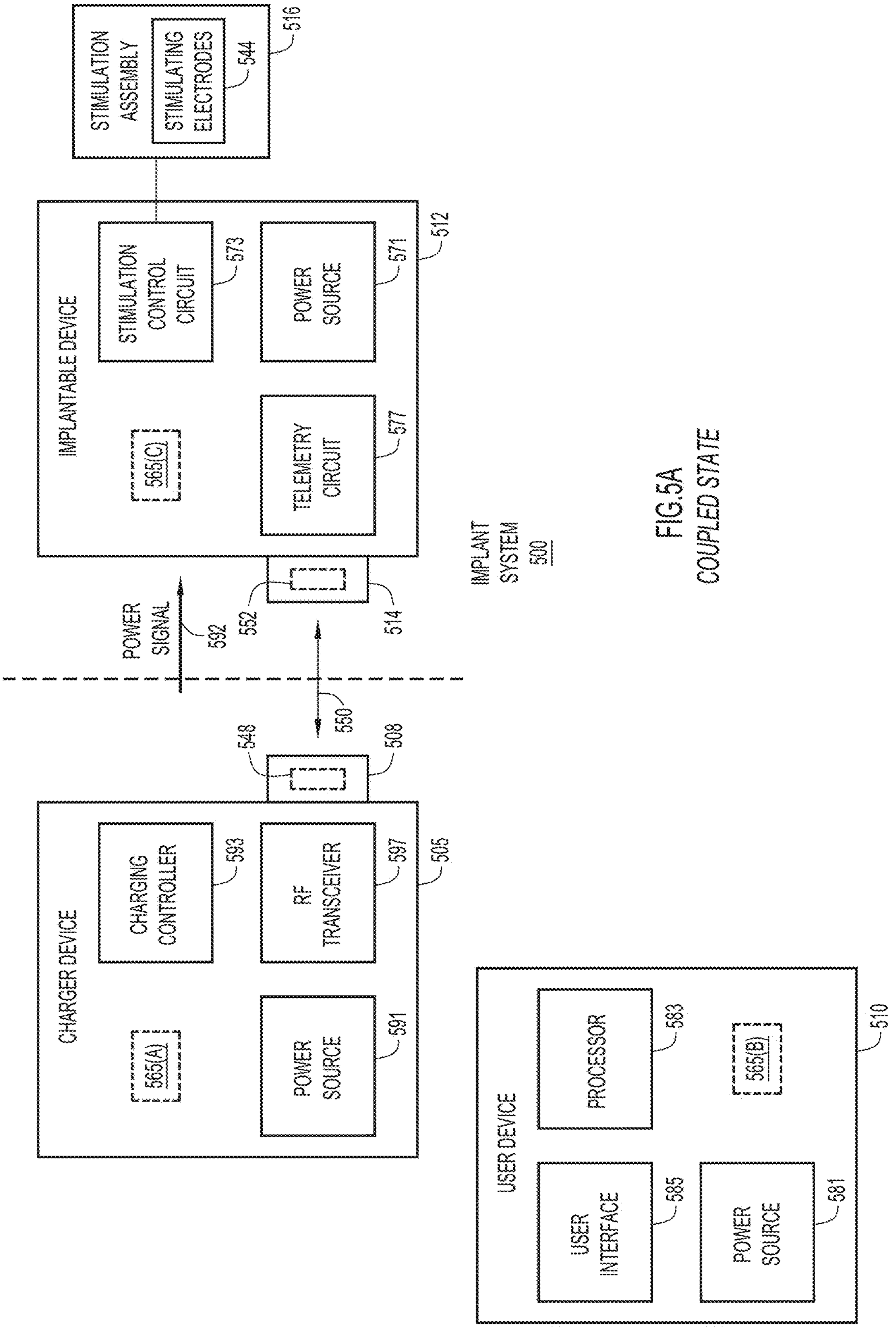
FIGS. 5A and 5B are functional block diagrams of an implant system operating with a user device, in accordance with certain embodiments presented herein.
Figure 5B:
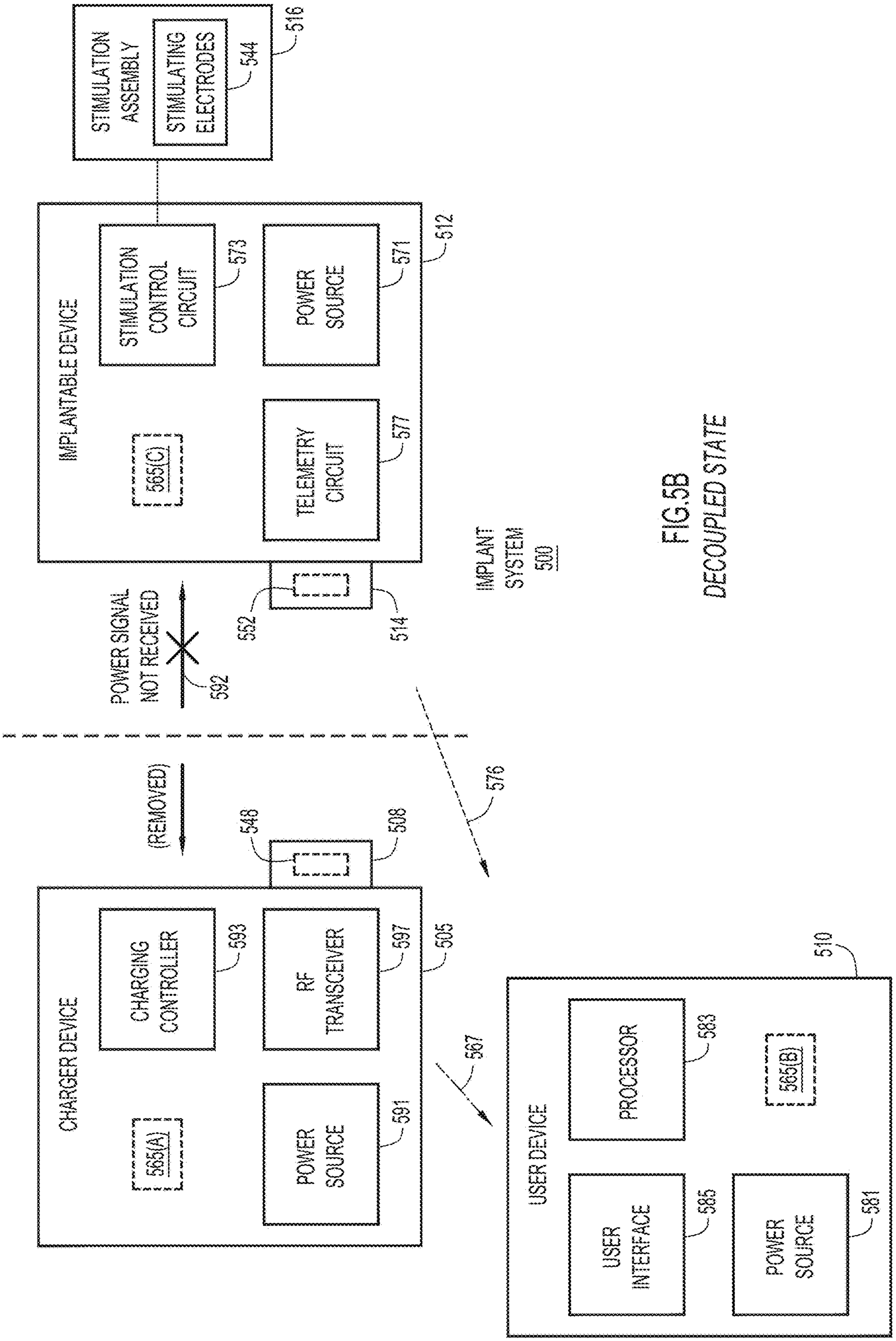

More specifically, FIGS. 5A and 5B are schematic diagrams illustrating a system 500 comprising an external component in the form of a charger device 505, an implantable component 512, and a user device 510. As described further below, in this example, the user device 510 is referred to as being "linked" or "associated" with the charger device 505 because the user device 510 is configured to as to be notified, either directly or indirectly, when the charger device 505 is decoupled from, or conversely when coupled to, the recipient.

In the specific examples of FIGS. 5A and 5B, the implantable device 512 comprises a rechargeable power source 571 (e.g., a battery, a capacitor, etc.), a stimulation control circuit 573, a power circuit 575, and a telemetry circuit 577. The implantable device 512 further comprises, or is connected with, a stimulation assembly 516 configured to be implanted in the user's head (under the skin/tissue). The stimulation assembly 516 includes one or more stimulating electrodes 544 (one or more electrical stimulating contact(s)) for delivery of electrical stimulation (current) to the user.

The stimulation control circuit 573 is configured to control electrical stimulation of a recipient (i.e., on-demand stimulation) via the one or more stimulating electrodes 544 of the stimulation assembly 516, potentially without the need for an external component (such as a sound processing unit) to control the stimulation. The stimulation control circuit 573 can comprise, for example, a processing unit and/or a stimulator unit. In certain embodiments, the stimulation control circuit 543 can be a relatively simple pulse generator circuit. The power circuit 575 is configured to charge the rechargeable power source 571 when the charger device 505 is present and the power signal 592 is received (refer to FIG. 5A).

The charger device 505 of FIG. 5A comprises a power source 591 (e.g., a rechargeable battery), a charging controller 593, and an RF transceiver 597. The charger device 505 of FIG. 5A is configured to charge the rechargeable power source 571 of the implantable device 512 with power (via a power signal 592) received transcutaneously from the charger device 505 by the implantable device 512. The charging controller 593 controls delivery of the power signal 592 from the power source 591 to the implantable device 512 via the RF transceiver 597 and a closely coupled wireless link 550 (e.g., RF link) formed between the external coil 508 and the implantable coil 514.

In the example of FIGS. 5A and 5B, the charger device 505 comprises an external coil 508 and an external magnet 548 fixed relative to the external coil 508, and the charger device 505 is configured to send power to the implantable device 512. The implantable device 512 comprises an implantable coil 514 and an internal magnet 552 fixed relative to the implantable coil 114. In general, the charger device 505 is a component that is configured to be magnetically coupled to the head of the user via the external magnet 548 and the internal magnet 552, and to be inductively coupled to the implantable device 512 via the external coil 508 and the implantable coil 514. The external magnet 548 and the internal magnet 552 facilitate "coupling" of the charger device 505 with the implantable device 512. When in a coupled state, as shown in FIG. 5A, the external coil 508 and the implantable coil 514 are in operational alignment and form the closely-coupled wireless link 550 for the transfer of power and, in certain examples, data between the charger device 505 with the implantable device 512. In certain embodiments, the closely-coupled wireless link 250 is a radio-frequency (RF) link. However, various other types of energy transfer, such as infrared (IR), electromagnetic, capacitive, and/or inductive transfer may be used to transfer the power from the charger device 505 to the implantable device 512.

Figure 5C:
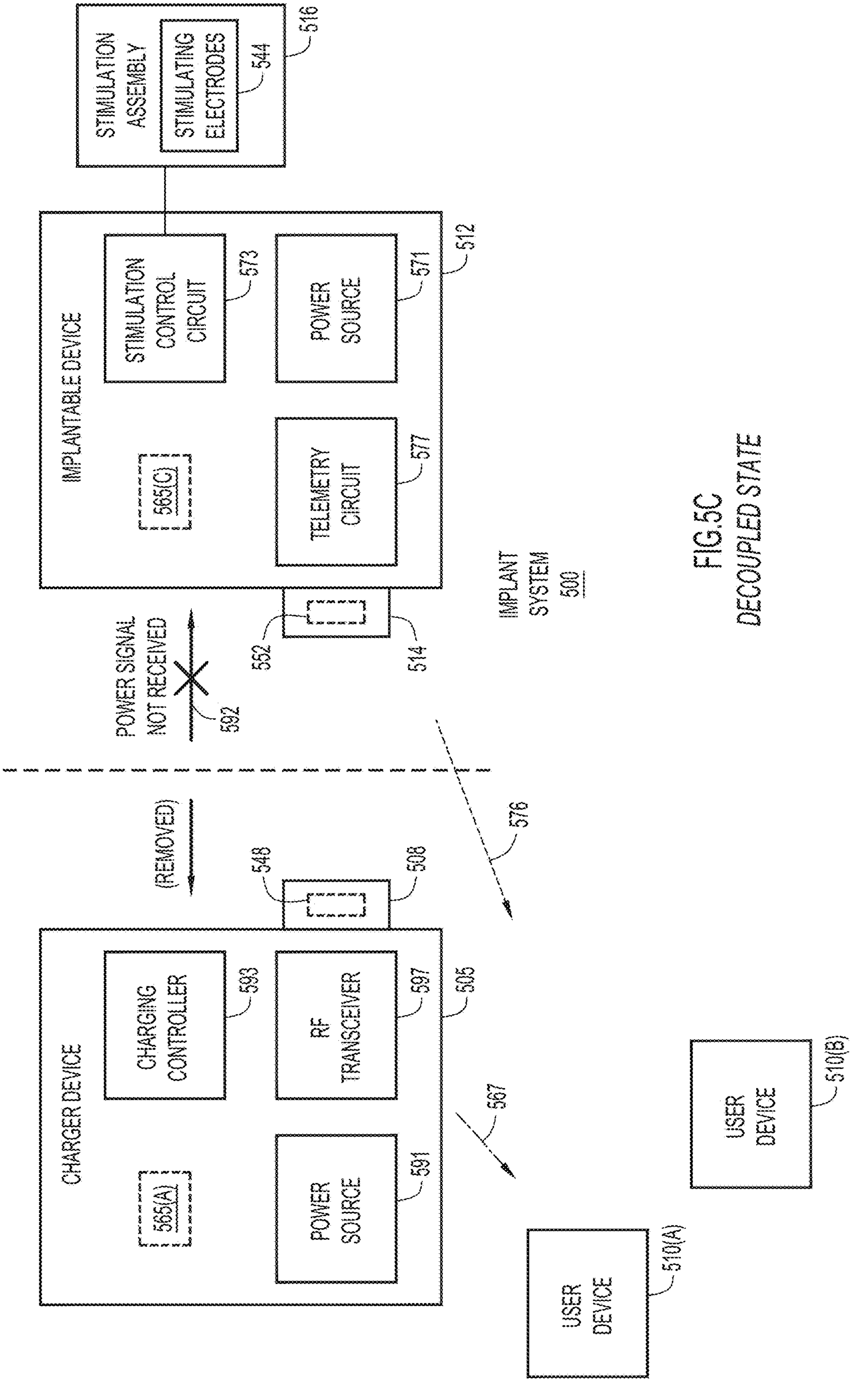
FIG. 5C is functional block diagram of an implant system operating with two user devices, in accordance with certain embodiments presented herein.

The user device 510 of FIGS. 5A and 5B can be a computing device, such as a wearable device (e.g., smartwatch), a mobile device (e.g., the recipient's smartphone, tablet, etc.), a remote-control unit (e.g., a dedicated implant controller), or other device with short-range wireless communications capabilities. In the example of FIG. 5C, the user device 510 comprises a power source 581 (e.g., a rechargeable battery), a processor 583, a user interface 585 module, and a wireless transceiver 587. The processor 583 can include one or more hardware or software processors (e.g., Central Processing Units) that can obtain and execute instructions. The processor 583 can communicate with and control the performance of other components of the user device 510. The user interface 585 module can include one or more input devices for receiving input from the user and one or more output devices for providing output to the user. The one or more input devices can include physically-actuatable user-interface elements (e.g., buttons, switches, dials), a keypad, a keyboard, a mouse, a touchscreen, a voice input device, etc. that can accept user input. The one or more output devices can include a display, one or more speakers, etc. for the presentation of visual or audible information to the user.

The user device 510 is configured to wirelessly communicate with the charger device 505 and/or the implantable device 512 via a short-range wireless communication protocol, such Bluetooth, Bluetooth Low Energy (BLE) link, a proprietary protocol, etc. To this end, shown in FIGS. 5A and 5B are wireless interfaces 565(A), 565(B), and 565(C) in the charger device 505, user device 510, and the implantable device 512, respectively. The wireless interfaces 565(A) and 565(C) are shown in dashed lines to indicate that those wireless interfaces may not be present in all embodiments.

As noted, FIG. 5A shows the charger device 505 in a "coupled state," e.g., where the external magnet 548 and the internal magnet 552 are magnetically coupled to one another. In contrast, FIG. 5B shows the charger device 505 in a "decoupled state," e.g., where the external magnet 548 and the internal magnet 552 are not magnetically coupled to one another. In accordance with embodiments presented herein, when the charger device 505 transitions from the coupled state of FIG. 5A to the decoupled state of FIG. 5B, or vice versa, the charger device 505 and/or the implantable device 512 sends a message/notification (indicated by dashed arrows 567) to the user device 510 indicating that the charger device 505 has transitions to the decoupled or coupled state. The notification 567 can be issued by charger device 505 and/or the implantable device 512, depending on which device has the ability to wirelessly communicate with the user device 510. That is, the charger device 505 and the user device 510 are referred to herein as being "linked" or "associated" with one another such that the user device 510 is notified, either directly or indirectly, when the charger device 505 is decoupled from, or conversely when coupled to, the recipient (thereby enabling the user device 510 to dynamically change how the device interacts with a user).

In accordance with embodiments presented herein, receipt of the notification 565 causes the user device 510 to dynamically adjust how it interacts with a user. More specifically, the user device 510 is configured to provide one type of user interaction while the charger device 505 is coupled to the recipient, but the user device 510 is configured to provide a different type of user interaction when the charger device 505 is decoupled from the recipient. In one example, the user device 510 dynamically adjusts a user interface provided by the user interface module 585, based on whether the charger device 505 is coupled or decoupled from the recipient. As noted elsewhere herein, a dynamic change in a user interface provided by the user interface module 585 is just one example of how a user device, such as user device 510, can dynamically change the interaction it provides with a user based on whether the external component is coupled to the recipient.

FIGS. 5A and 5B illustrate an example in which one user device 510 operates with the implant system 500. FIG. 5C illustrates another embodiment in which at least two user devices, referred to as user devices 510(A) and 510(B) operate with the implant system 500. For case of illustration, user devices 510(A) and 510(B) are shown in FIG. 5C in a simplified form, but it would be appreciated that the user devices 510(A) and 510(B) could each have similar components to user device 510 of FIGS. 5A and 5B.

In this embodiment, when the charger device 505 transitions from the coupled state of FIG. 5A to the decoupled state of FIG. 5B, or vice versa, the charger device 505 and/or the implantable device 512 sends a message/notification (indicated by dashed arrows 567) to one or both of the user devices 510(A) and 510(B) indicating that the charger device 505 is in the decoupled state. The notification 567 can be issued by charger device 505 and/or the implantable device 512, depending on which device has the ability to wirelessly communicate with the user devices 510(A) and/or 510(B). The notification 567 could be received at both user devices 510(A) and 510(B), or at only one of the user devices 510(A) and 510(B). In the later scenario, the user device that receives the notification could, in turn, notify the other user device of the change in coupling states.

In accordance with embodiments presented herein, receipt of the notification 565 causes the user devices 510(A) and 510(B) to each dynamically adjust how it interacts with a user. More specifically, the user devices 510(A) and 510(B) are each configured to provide one type of user interaction while the charger device 505 is coupled to the recipient, but the user devices 510(A) and 510(B) are each configured to provide a different type of user interaction when the charger device 505 is decoupled from the recipient. In one example, the user devices 510(A) and 510(B) dynamically adjust a user interface provided by their respective user interface modules 585, based on whether the charger device 505 is coupled or decoupled from the recipient.

The use of two user devices 510(A) and 510(B), as shown in FIG. 5C, is merely illustrative and other numbers of user devices could be used in other embodiments. In addition, various combinations or groups of user devices could be used in different embodiments. For example, the user devices 510(A) and 510(B) could comprise a mobile device and wearable device that each operate with the implant system 500.

As noted, FIGS. 2, 3, and 4 also generally illustrate examples in which an external component itself is configured to provide a different type of user interaction depending on whether or not the external component is coupled to, or decoupled from, the recipient. In addition, FIGS. 5A, 5B, and 5C illustrate examples in which a user device that is linked/associated with an external component is configured to provide a different type of user interaction depending on whether or not the associate external component is coupled to, or decoupled from, the recipient. As noted above, external components and user devices are collectively and generally referred to herein as recipient-associated devices. In addition, also as noted above, the term linked recipient-associated device includes the external component that is coupled/decoupled from the recipient, as well as any separate devices that are linked to the external component that is coupled/decoupled (i.e., associated such that the separate device is notified when the component that is coupled/decoupled from the recipient). The following descriptions provides examples of how a linked recipient-associated device, whether it is an external component, a mobile phone, a smartwatch, etc., can dynamically adjust how it interacts with user based on whether the associated/liked external component is coupled or decoupled from a recipient).

In general, the techniques are described herein with reference to a "direct" link between an external component and another device. However, it is to be appreciated that the techniques presented herein could be implemented with an "indirect" link (e.g., the link could go through one or more intermediary devices, such as a remote server (cloud) which may or may not involve processing before a change in user interface or notification is received).

In certain embodiments, while the external component is coupled to recipient, the linked recipient-associated devices can provide information about the implantable component (e.g., implant status, battery information, etc.). However, when the external component is decoupled from the recipient, the linked recipient-associated device can display, at least temporarily, information that is not related to the implantable component (e.g., information about the external component, such as battery life, connection status, etc., information about the recipient, etc.). For example, in one such embodiment in which the external component is a charger, the user interface module of the charger could display, while coupled to the recipient, charging progress or time until the implant battery is charged. However, when the charger is decoupled from the recipient, the user interface module of the charger could display remnant charge of charger (e.g., percentage, light for low battery, etc.), recipient information, etc. In other charger examples, while coupled to the recipient, the charger and an associated phone could each display the time remaining until full charge of the implant battery, but each display different information when the charger is decoupled.

In another example in which the external component is a charger, the charger could be configured to, when coupled to the recipient, provide a user with control options to change settings/parameters related to charging of the implant (e.g., charging speed or other settings, check charging status, etc.). However, when the charger is decoupled from the recipient, the charger presents different control options that enable the user to adjust parameters/settings of the charger itself.

In one example, when an external component is coupled to a mobile phone and an implantable component, the user interface module of the external component could allow for a button press or other user intervention to answer and stream a phone call, pause/play music, etc. However, when the external component is decoupled from the mobile phone or the implantable component, this type of button press/intervention is disabled.

In one example of a non-hearing wearable device, a change of an external component from coupled to decoupled could initiate a user interface change that instructs the user to re-couple the external component to the recipient. The interface change could be a haptic output at the external component, a notification issued via a mobile phone or other linked recipient-associated device, etc. (e.g., trigger a phone prompt just to let the user know the external component has been decoupled, which may not be obvious for certain types of devices).

In certain embodiments, coupling or decoupling of an external component to/from a recipient could trigger a so-called "transient mode" where a certain interaction is only provided for a period of time substantially immediately after coupling or decoupling. For example, a linked recipient-associated device could be configured to provide a "transient display" of information about the implantable component for only a period of time (e.g., 10 seconds) after the external component is decoupled from the recipient. Thereafter, the recipient-associated device could terminate the transient display and display other information. That is, in these embodiments, the recipient-associated device could provide a first informational display for a period of time substantially immediately after coupling or decoupling of the external component, and then provide a second informational display thereafter.

Figure 6:
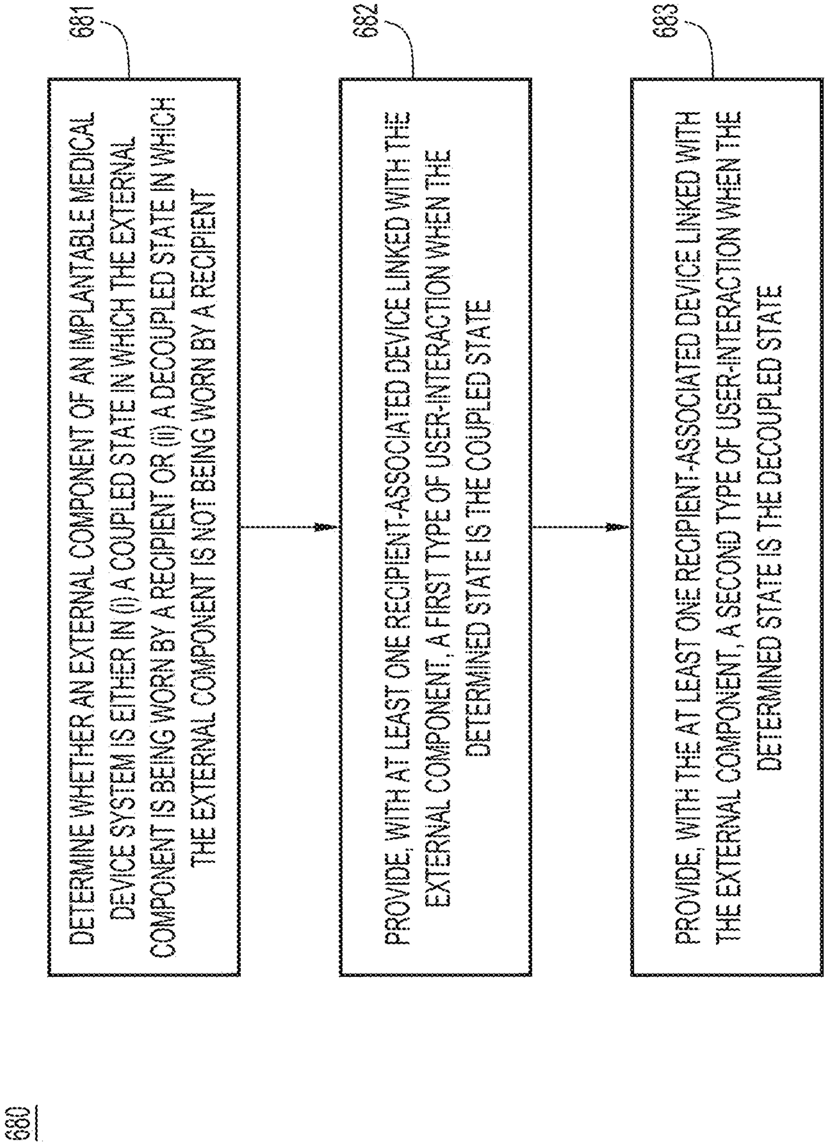
FIG. 6 is a flowchart of an example method, in accordance with certain embodiments presented herein.

FIG. 6 is a flowchart of an example method 680, in accordance with certain embodiments presented herein. Method 680 begins at 681 with a determination of whether an external component of an implantable medical device system is either in (i) a coupled state in which the external component is being worn by a recipient or (ii) a decoupled state in which the external component is not being worn by a recipient (e.g., a determination as to whether or not an external component is coupled to a recipient). As described elsewhere herein, this determination can be made in a number of different ways and can be made by a number of different devices (e.g., the external component or other linked recipient-associated device, an implantable component, etc.).

At 682, when the determined state is the coupled stated, the method includes providing, with at least one recipient-associated device linked with the external component, a first type of user-interaction. At 683, when the determined state is the decoupled state, the method includes providing, with the at least one recipient-associated device linked with the external component, a second type of user-interaction. As described elsewhere herein, the "at least one recipient-associated device linked with the external component," sometimes referred to elsewhere wherein as the "linked recipient-associated device" includes the external component itself or one or more separate second devices that are linked/associated with the external component.

In one example of FIG. 6, wherein providing the first type of user-interaction comprises providing, via a user interface component, a first user interface when the determined state is the coupled state, while wherein providing the second type of user-interaction comprises providing, via the user interface component, a second user interface when the determined state is the decoupled state, wherein the second user interface is different from the first user interface. However, as described elsewhere herein, the first and second types of user-interactions can alternatively take a number of different forms.

Figure 7:
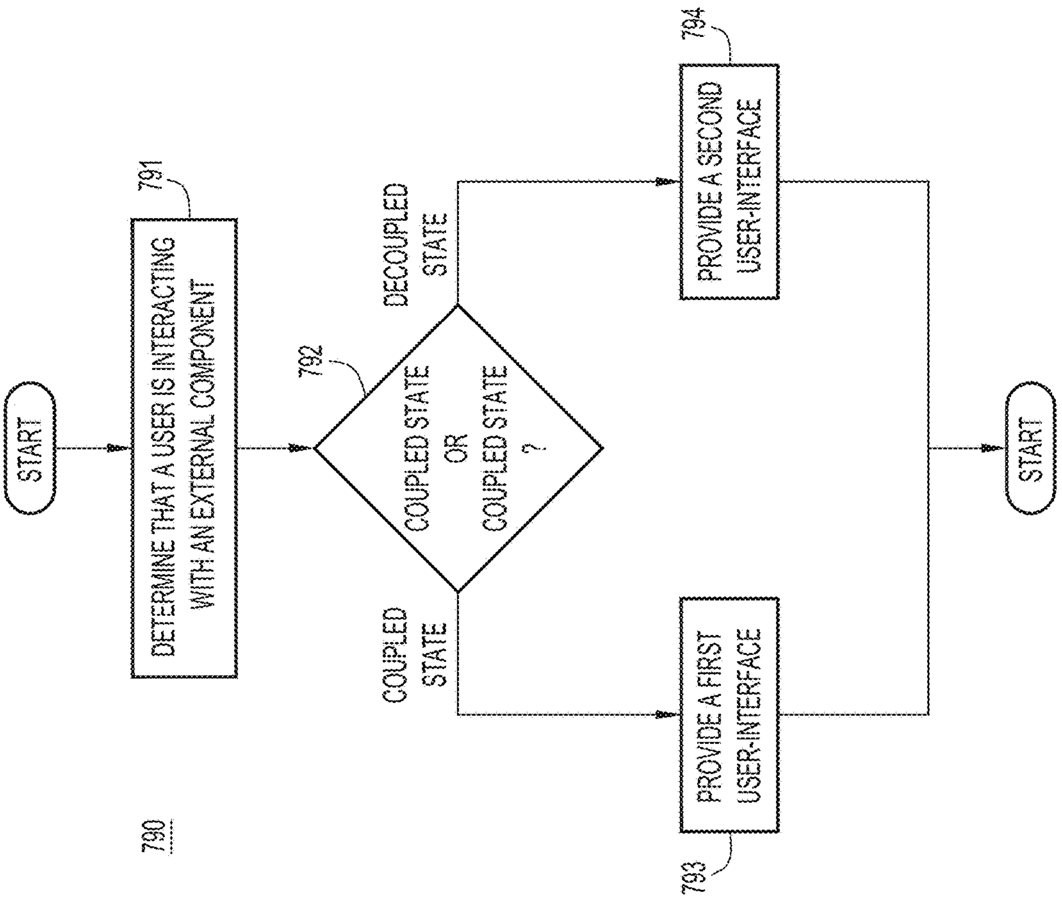
FIG. 7 is a flowchart of another example method, in accordance with certain embodiments presented herein.

Shown in FIG. 7 is another flow chart of a method 790 that can be carried out by an external component of an implantable medical device system, in accordance with certain embodiments presented herein. For purposes of illustration only, these functions will be described with reference to cochlear implant system 102 of FIGS. 1A-1D.

As shown in FIG. 7, the method 790 begins at step 791 with the external component 104 determining that a recipient is interacting with the external component 104. The external component 104 may make this determination in any number of ways. As one example, if the recipient interacts with a user-input component, then the external component 104 determines that the recipient is interacting with the external component 104. As another example, the external component 104 may determine that a movement of the external component 104 is consistent with a recipient interaction. For instance, the external component 104 may include one or more sensors, such as one or more accelerometers. When the recipient decouples the external component 104 from the cochlear implant 112, or perhaps picks the external component 104 up from a table, the one or more sensors may each provide signal indicative of a movement, which the external component 104 could interpret as a recipient interaction. To this end, the external component 104 may process each signal received from the one or more sensors to determine whether a detected movement exceeds a threshold. If the external component 104 determines that the detected movement exceeds the threshold, the external component 104 may determine that the movement is consistent with a recipient interaction. Or the external component 104 may determine whether the recipient is interacting with the external component 104 based on a signal received from a different sensor, such as a camera or an infrared light emitter/detector, configured to provide an output when the recipient is looking at the external component 104. Such sensor could provide an output when the recipient is looking at a visual-output component of the external component 104, and the external component 104 may responsively determine that the output is indicative of a recipient interaction.

The method 790 continues at 792 with the external component 104 making a determination of whether the external component 104 and the cochlear implant 112 are coupled or decoupled. The external component 104 may make this determination in one of several ways. As noted above, the cochlear implant 112 may periodically transmit telemetry data to the external component 104 at regular intervals. As a result, the external component 104 can determine the state based on a time since telemetry data was last received. If the external component 104 receives telemetry data within a given period of time, such as 200 milliseconds or even as long as 1 second, the external component 104 may then determine that the external component 104 and the cochlear implant 112 are coupled. If on the other hand the external component 104 has not received telemetry data within such a period of time, the external component 104 may then determine that the external component 104 and the cochlear implant 112 are decoupled.

In an alternative example, the external component 104 could make the determination based on a signal provided by a sensor configured to detect a magnetic field, such as a Reed switch or a Hall effect sensor. In practice, for instance, the sensor could provide an output when the external component 104 is coupled to cochlear implant 112, whereas the sensor might not provide an output when external component 104 is decoupled from the cochlear implant 112. The external component 104 may thus make the determination based on the whether the sensor provides the output.

If the determination is that the state is the coupled state, then the method 790 continues, at 793, with the external component 104 providing a first user interface. On the other hand, if the determination at 792 is that the external component 104 is decoupled from the cochlear implant 112, then the method 790 continues at 794 with the external component 104 providing a second user interface.

In line with the discussion above, the functionalities provided by the first user interface differ from the functionalities provided by the second user interface. For instance, the functionalities provided by the first user interface could include providing each of a first set of functions and a first set of visual outputs, while the functionalities provided by second user interface could include providing each of a second set of functions and a second set of visual outputs. As described above, in certain examples, the functionalities of the second set user interface-which is provided in the decoupled state-provide the recipient with access to settings of more parameters than are provided by functionalities of the first user interface. But while the first set of functions differs from the second set of functions, each user interface provides at least one functionality for changing a setting of a sound-processing parameter. Similarly, the second set of visual outputs includes a greater number of visual outputs than the first set of visual outputs. That is, both the first set of functions and the second set of functions may include one or more common functions, such as the ability to adjust a volume of perceived sounds or to change a sound-processing profile.

After performing the steps of either 793 or 794, the method 790 ends. Note that, in some examples, the external component 104 may not perform the steps of the method 790 in the order described. For instance, the external component 104 could perform the steps of 792, and then perform the steps of block 791 before proceeding to either 793 or 794. Or the external component 104 may omit step 791 altogether. Moreover, the external component 104 may periodically perform one or more operations of the method 790 to verify that the external component 104 is operating in the correct state. Additionally or alternatively, the external component 104 may perform one or more blocks of the method 790 in response to receiving an indication of a change of state, such as a signal from a sensor, an indication of the external component's battery charging, etc.

As noted, certain aspects of the techniques presented herein have described herein with reference to a "direct" link between an external component and another device. However, it is to be appreciated that the techniques presented herein could be implemented with an "indirect" link (e.g., the link could go through one or more intermediary devices, such as a remote server (cloud) which may or may not involve processing before a change in user interface or notification is received).

As previously described, the technology disclosed herein can be applied in any of a variety of circumstances and with a variety of different devices. Example devices that can benefit from technology disclosed herein are described in more detail in FIGS. 8 and 9. The techniques of the present disclosure can be applied to other devices, such as neurostimulators, cardiac pacemakers, cardiac defibrillators, sleep apnea management stimulators, seizure therapy stimulators, tinnitus management stimulators, and vestibular stimulation devices, as well as other medical devices that deliver stimulation to tissue. Further, technology described herein can also be applied to consumer devices. These different systems and devices can benefit from the technology described herein.

Figure 8:
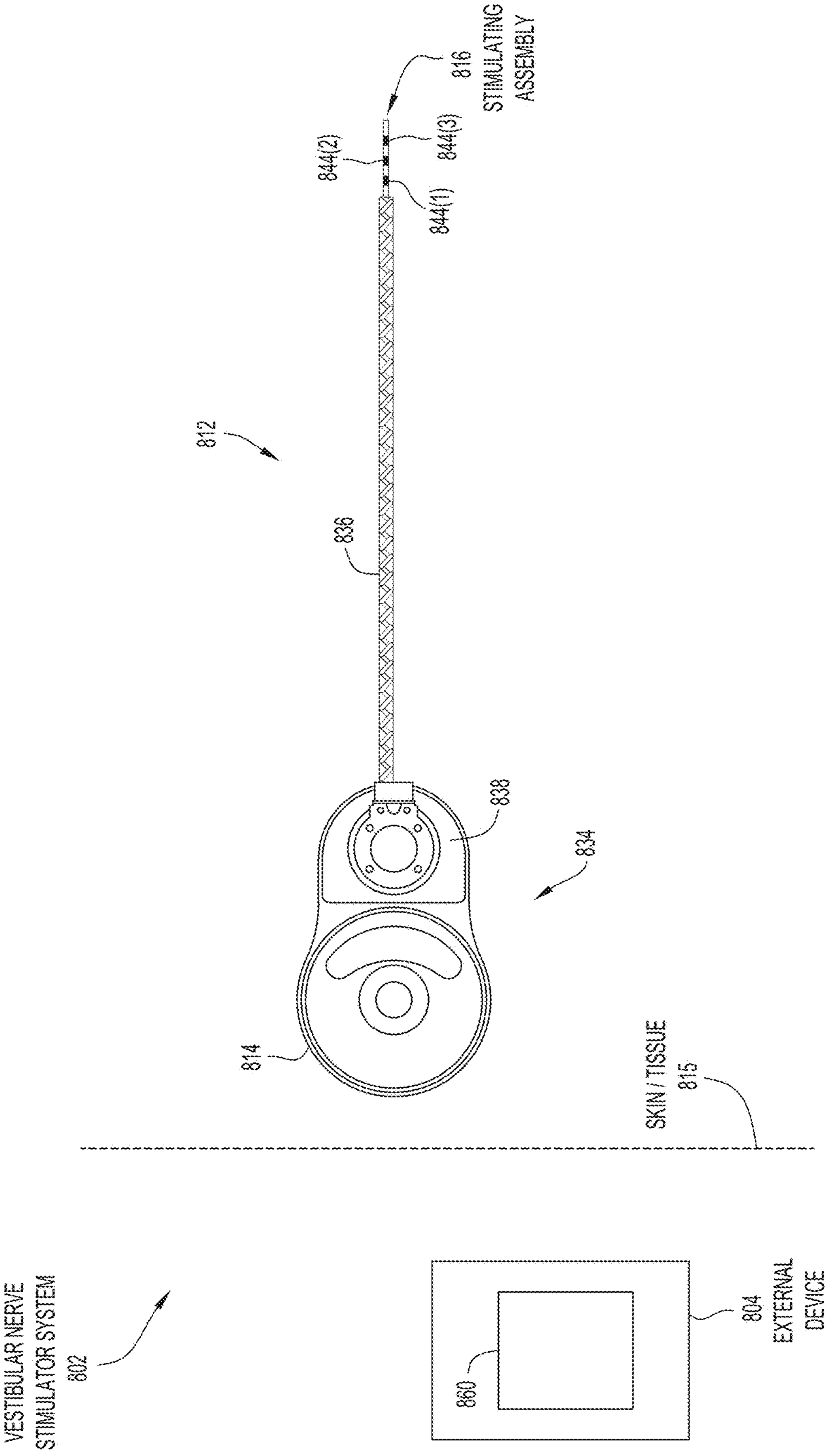
FIG. 8 is a schematic diagram illustrating a vestibular stimulator system with which aspects of the techniques presented herein can be implemented.

FIG. 8 illustrates an example vestibular stimulator system 802, with which embodiments presented herein can be implemented. As shown, the vestibular stimulator system 802 comprises an implantable component (vestibular stimulator) 812 and an external device/component 804 (e.g., external processing device, battery charger, remote control, etc.). The external device 804 comprises a transceiver unit 860. As such, the external device 804 is configured to transfer data (and potentially power) to the vestibular stimulator 812.

The vestibular stimulator 812 comprises an implant body (main module) 834, a lead region 836, and a stimulating assembly 816, all configured to be implanted under the skin/tissue (tissue) 815 of the recipient. The implant body 834 generally comprises a hermetically-sealed housing 838 in which RF interface circuitry, one or more rechargeable batteries, one or more processors, and a stimulator unit are disposed. The implant body 134 also includes an internal/implantable coil 814 that is generally external to the housing 838, but which is connected to the transceiver via a hermetic feedthrough (not shown).

The stimulating assembly 816 comprises a plurality of electrodes 844(1)-(3) disposed in a carrier member (e.g., a flexible silicone body). In this specific example, the stimulating assembly 816 comprises three (3) stimulation electrodes, referred to as stimulation electrodes 844(1), 844(2), and 844(3). The stimulation electrodes 844(1), 844(2), and 844(3) function as an electrical interface for delivery of electrical stimulation signals to the recipient's vestibular system.

The stimulating assembly 816 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

In operation, the vestibular stimulator 812, the external device 804, and/or another external device can be configured to implement the techniques presented herein. That is, the vestibular stimulator 812, possibly in combination with the external device 804 and/or another external device, can include an evoked biological response analysis system, as described elsewhere herein.

Figure 9:
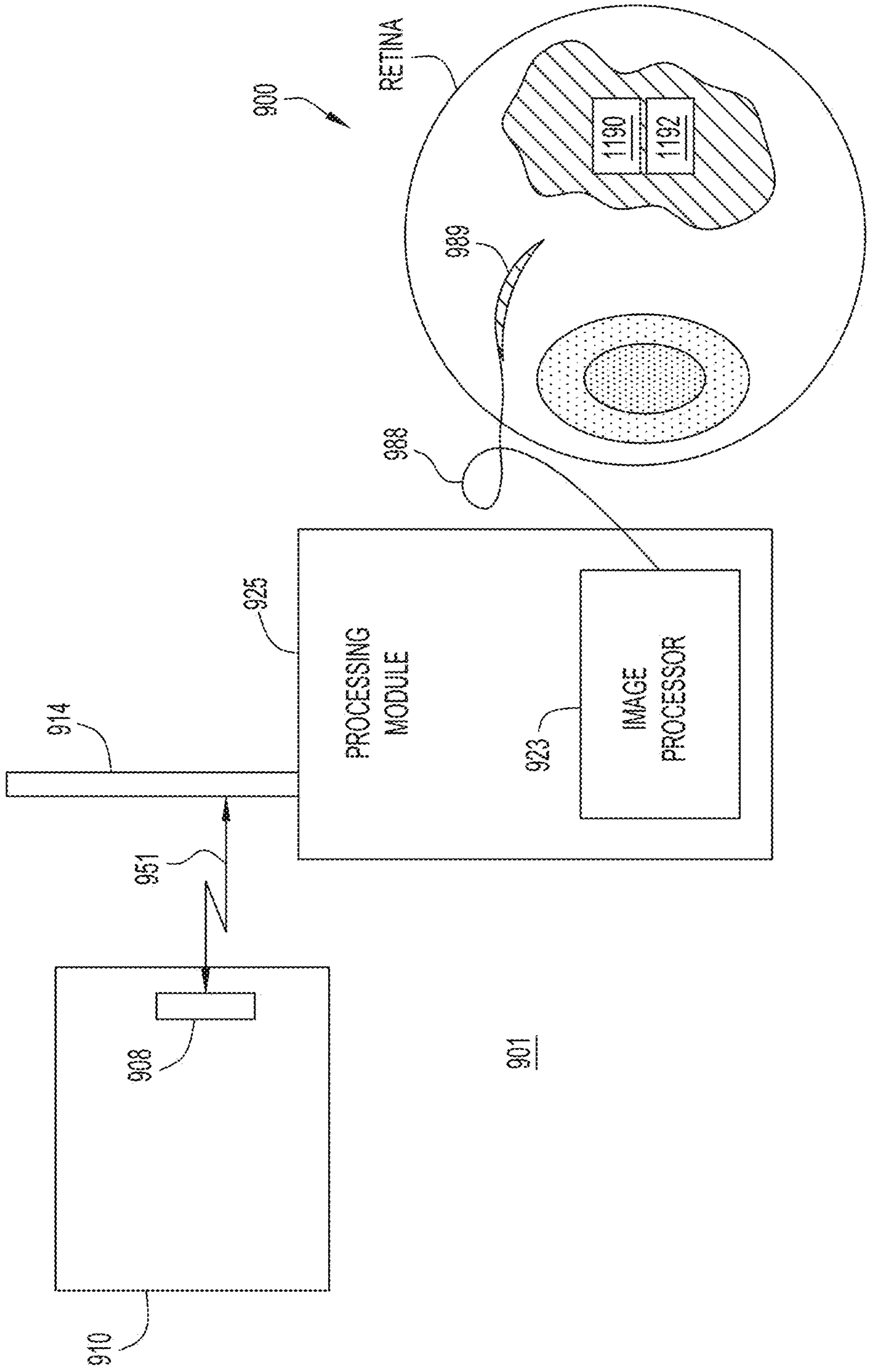
FIG. 9 is a schematic diagram illustrating a retinal prosthesis system with which aspects of the techniques presented herein can be implemented.

FIG. 9 illustrates a retinal prosthesis system 901 that comprises an external device 910 (which can correspond to the wearable device 100) configured to communicate with an implantable retinal prosthesis 900 via signals 951. The retinal prosthesis 900 comprises an implanted processing module 925, and a retinal prosthesis sensor-stimulator 990 is positioned proximate the retina of a recipient. The external device 910 and the processing module 925 can communicate via coils 908, 914.

In an example, sensory inputs (e.g., photons entering the eye) are absorbed by a microelectronic array of the sensor-stimulator 990 that is hybridized to a glass piece 992 including, for example, an embedded array of microwires. The glass can have a curved surface that conforms to the inner radius of the retina. The sensor-stimulator 990 can include a microelectronic imaging device that can be made of thin silicon containing integrated circuitry that convert the incident photons to an electronic charge.

The processing module 925 includes an image processor 923 that is in signal communication with the sensor-stimulator 990 via, for example, a lead 988 that extends through surgical incision 989 formed in the eye wall. In other examples, processing module 925 is in wireless communication with the sensor-stimulator 990. The image processor 923 processes the input into the sensor-stimulator 990 and provides control signals back to the sensor-stimulator 990 so the device can provide an output to the optic nerve. That said, in an alternate example, the processing is executed by a component proximate to, or integrated with, the sensor-stimulator 990. The electric charge resulting from the conversion of the incident photons is converted to a proportional amount of electronic current which is input to a nearby retinal cell layer. The cells fire and a signal is sent to the optic nerve, thus inducing a sight perception.

The processing module 925 can be implanted in the recipient and function by communicating with the external device 910, such as a BTE unit, a pair of eyeglasses, etc. The external device 910 can include an external light/image capture device (e.g., located in/on a behind-the-ear device or a pair of glasses, etc.), while, as noted above, in some examples, the sensor-stimulator 990 captures light/images, in which sensor-stimulator 990 is implanted in the recipient.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

According to certain aspects, systems and non-transitory computer readable storage media are provided. The systems are configured with hardware configured to execute operations analogous to the methods of the present disclosure. The one or more non-transitory computer readable storage media comprise instructions that, when executed by one or more processors, cause the one or more processors to execute operations analogous to the methods of the present disclosure.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

It is also to be appreciated that the embodiments presented herein are not mutually exclusive and that the various embodiments may be combined with another in any of a number of different manners.

The invention claimed is:

1. A method comprising:

determining whether a state of an external unit of a hearing device is one of (i) a coupled state when the external unit and a stimulation unit of the hearing device are coupled or (ii) a decoupled state when the external unit and the stimulation unit are decoupled; and providing by the external unit one of (i) a first user interface when the determined state is the coupled state or (ii) a second user interface when the determined state is the decoupled state, wherein the second user interface provides access to a greater number of functions of the hearing device than the first user interface provides.

2. The method of claim 1, wherein:

providing the first user interface comprises selecting a first visual output from a first set of visual outputs and causing a visual-output component of the external unit to display the first visual output, and providing the second user interface comprises selecting a second visual output from a second set of visual outputs and causing the visual-output component to display the second visual output, wherein the second set of visual outputs comprises a greater number of visual outputs than the first set of visual outputs.

3. The method of claim 2, wherein the visual-output component includes at least one LED, the first set of visual outputs includes a visual output in which the at least one LED illuminates in one or more colors to provide an indication of whether the hearing device is properly functioning, and the second set of visual outputs includes a visual output in which the at least one LED illuminates in a pattern or a sequence indicative of at least one of (1) a status of a component of the hearing device or (2) a sound-processing parameter used by a sound processor of the hearing device.

4. The method of claim 1, wherein providing the first user interface and the second user interface comprises:

receiving at the external unit a user input that includes a change to a setting of a selected sound-processing parameter, wherein the sound-processing parameter is used by a sound processor of the hearing device to either process sounds or generate stimulation signals, and wherein more sound-processing parameters are selectable when the external unit provides the second user interface than when the external unit provides the first user interface; and processing the user input to apply the change to the selected sound-processing parameter.

5. The method of claim 4, wherein each sound-processing parameter that is selectable when the external unit provides the first user interface is selectable when the external unit provides the second user interface.

6. The method of claim 1, wherein providing the second user interface comprises:

receiving at the external unit a user input that includes a selection of a system parameter, wherein the system parameter is directed to a function of the hearing device unrelated to sound-processing, and processing the user input to identify a status of the system parameter; and providing a visual output of the identified status.

7. The method of claim 1, wherein, when the determined state is the decoupled state, the method further comprises making a determination of whether the external unit received a user interaction within a period of time, wherein providing the second user interface comprises:

providing a visual output indicative of the external unit being idle when the determination is that the external unit did not receive the user interaction within the period of time; and providing a visual output that includes a display of information when the determination is that the external unit received the user interaction within the period of time.

8. The method of claim 7, wherein the user interaction is one of an input received at a user input component of the external unit or an indication that an individual is looking a at visual-output component of the external unit.

* * * * *